US012605327B2

(12) United States Patent
Ye-Tse et al.

(10) Patent No.: US 12,605,327 B2
(45) Date of Patent: Apr. 21, 2026

(54) HAIR COSMETIC COMPOSITIONS

(71) Applicant: L'OREAL, Paris (FR)

(72) Inventors: Lisa Chuyin Ye-Tse, Brooklyn, NY (US); Seyma Aslan, Clifton, NJ (US); XianZhi Zhou, Millburn, NJ (US); Rita Chokshi, Monroe Township, NJ (US)

(73) Assignee: L'OREAL, Paris (FR)

(*) Notice: Subject to any disclaimer, the term of this patent is extended or adjusted under 35 U.S.C. 154(b) by 28 days.

(21) Appl. No.: 17/187,819

(22) Filed: Feb. 28, 2021

(65) Prior Publication Data

US 2022/0273551 A1 Sep. 1, 2022

(51) Int. Cl.

| | |
|---|---|
| ***A61K 8/891*** | (2006.01) |
| ***A61K 8/06*** | (2006.01) |
| ***A61K 8/34*** | (2006.01) |
| ***A61K 8/37*** | (2006.01) |
| ***A61K 8/60*** | (2006.01) |
| ***A61K 8/73*** | (2006.01) |
| ***A61K 8/81*** | (2006.01) |
| ***A61K 8/86*** | (2006.01) |
| ***A61K 8/892*** | (2006.01) |
| ***A61K 8/92*** | (2006.01) |
| ***A61Q 5/06*** | (2006.01) |

(52) U.S. Cl.

CPC .............. *A61K 8/891* (2013.01); *A61K 8/062* (2013.01); *A61K 8/342* (2013.01); *A61K 8/345* (2013.01); *A61K 8/37* (2013.01); *A61K 8/608* (2013.01); *A61K 8/737* (2013.01); *A61K 8/8147* (2013.01); *A61K 8/8182* (2013.01); *A61K 8/86* (2013.01); *A61K 8/892* (2013.01); *A61K 8/922* (2013.01); *A61Q 5/06* (2013.01); *A61K 2800/5422* (2013.01)

(58) Field of Classification Search

None

See application file for complete search history.

(56) References Cited

U.S. PATENT DOCUMENTS

| | | | | |
|---|---|---|---|---|
| 4,719,104 A * | 1/1988 | Patel | A61K 8/416 | 424/70.28 |
| 4,749,732 A * | 6/1988 | Kohl | A61K 8/898 | 524/46 |
| 8,475,778 B2 | 7/2013 | Van Nguyen et al. | | |
| 10,555,891 B2 | 2/2020 | Patterson et al. | | |
| 10,821,067 B2 | 11/2020 | Perner et al. | | |
| 2003/0039671 A1* | 2/2003 | Tournilhac | A61K 8/044 | 424/401 |
| 2003/0191035 A1* | 10/2003 | Verboom | A61K 8/416 | 424/70.14 |
| 2004/0170586 A1* | 9/2004 | Ferrari | A61Q 19/00 | 424/63 |
| 2007/0184002 A1* | 8/2007 | Vrignaud | A61Q 5/06 | 424/70.13 |
| 2011/0224309 A1* | 9/2011 | Hunter | A61K 8/39 | 514/777 |
| 2013/0177516 A1* | 7/2013 | Tamura | A61K 8/893 | 8/405 |
| 2013/0315846 A1 | 11/2013 | Collier et al. | | |
| 2015/0250711 A1 | 9/2015 | Nguyen et al. | | |
| 2016/0175237 A1 | 6/2016 | Shin et al. | | |
| 2017/0189306 A1 | 7/2017 | Van Nguyen et al. | | |
| 2018/0280267 A1* | 10/2018 | Rughani | A61K 8/362 | |
| 2019/0125650 A1 | 5/2019 | Lee et al. | | |

FOREIGN PATENT DOCUMENTS

| | | | | |
|---|---|---|---|---|
| CA | 2328997 A1 * | 10/1999 | | |
| CN | 106806165 A | 6/2017 | | |
| DE | 102016225046 A1 | 8/2017 | | |
| EP | 0489581 A2 * | 6/1992 | | |
| WO | WO-2010049434 A2 * | 5/2010 | | A61K 8/042 |
| WO | WO-2016098786 A1 * | 6/2016 | | A61K 8/062 |

OTHER PUBLICATIONS

Dow Corning, Product Information: Dow Corning® FA 4002 ID Silicone Acrylate, Mar. 25, 2009 (Year: 2009).*

Lovelyn et al., Current State of Nanoemulsions in Drug Delivery, Journal of Biomaterials and Nanobiotechnology, 2011, 2, 626-639 (Year: 2011).*

Fevola, Cosmetics and Toiletries: Polyquaternium-6, https://www.cosmeticsandtoiletries.com/cosmetic-ingredients/moisturizing/article/21834683/ingredient-profile-polyquaternium-6, Mar. 2, 2011 (Year: 2011).*

Preliminary Search Report and Written Opinion issued on Jul. 19, 2022 for corresponding French Application No. FR 2107897.

* cited by examiner

*Primary Examiner* — Jennifer A Berrios

(74) *Attorney, Agent, or Firm* — POLSINELLI PC

(57) ABSTRACT

Aspects of the disclosure are directed to a hair cosmetic composition comprising: about 4 to about 32 wt. % of two or more polyols, such as about 1 wt. % or more of a glycol and about 2 wt. % or more of glycerin; about 0.5 to about 10 wt. % of a nonionic surfactant; about 2 to about 35 wt. % of a fatty ester; about 0.1 to about 7 wt. % of a film former; about 0.05 to about 10 wt. % of a silicone polymer; about 0.5 to about 12 wt. % of an oil; and water, wherein all weight percentages are based on the total weight of the hair cosmetic composition.

17 Claims, 3 Drawing Sheets

HAIR COSMETIC COMPOSITIONS

FIELD OF THE DISCLOSURE

The instant disclosure relates to hair cosmetic compositions providing a unique sensorial experience. Additionally, aspects of the disclosure are related to hair cosmetic compositions that provide conditioning and other benefits to the hair.

BACKGROUND OF THE DISCLOSURE

Many consumers desire to use cosmetic and care compositions that enhance the appearance of keratinous substrates such as hair, e.g., by changing, style, shape, and/or by imparting various cosmetic properties to hair. Different types of hair styling products have been developed by manufacturers that aim to help consumers achieve a desired look, including stylized hair that is long-lasting. Such hair styling products are typically provided in a variety of physical forms, such as liquid, gel, mousse, or pomade, depending on the composition, styling/setting performance, consumer acceptance, branding, and marketing, amongst other variables. Many traditional hair styling products ignore and, sometimes, even reduce desired hair properties, such as sleekness, shine, amount of conditioning, closed-ends, and the like.

While different technologies and products exist in the market for hair styling products, there is still a need for improvement in these areas as well as at the same time, the need to provide caring benefits that are not typically found in a styling product.

SUMMARY OF THE DISCLOSURE

Aspects of the instant disclosure relate to hair cosmetic compositions providing a unique sensorial experience. The hair cosmetic compositions are typically formulated to include specific ingredients in certain amounts and ratios, such that the hair cosmetic compositions provide a unique sensor experience. In particular, certain embodiments of the disclosure provide hair cosmetic compositions in the form of a cream that transforms into an oil before or during application of the hair cosmetic compositions onto hair. For instance, as the user rubs, spreads, and/or shears the hair cosmetic composition on dry or wet hand(s) or applies the composition directly to dry or wet hair (e.g., by rubbing, spreading and/or massaging the cream on the hair fibers), the cream transforms into an oil.

Without being limited to any specific theory, it is believed that the shear stress associated with the application of the hair cosmetic compositions breaks the emulsion associated with the hair cosmetic composition to, at least partly, contribute to the transformation of the hair cosmetic composition from a cream to an oil. Accordingly, in some instances, the transformation of the hair cosmetic composition from a cream to an oil refers to the hair cosmetic composition transforming from having rheological properties and/or a tactile feel associated with a cream to having rheological properties and/or a tactile feel associated with an oil. Additionally, the inventor's surprisingly discovered that the transformation of the hair cosmetic compositions from a cream to an oil deposits certain ingredients to the user's hair and scalp to provide enhanced benefits, such as conditioning benefits.

The hair cosmetic compositions, according to an aspect of the disclosure, typically comprise:

(a) about 4 to about 32 wt. % of two or more polyols comprising:
 (i) about 1 wt. % or more of a glycol, and
 (ii) about 2 wt. % or more of glycerin;
(b) about 0.5 to about 10 wt. % of a nonionic surfactant;
(c) about 2 to about 35 wt. % of a fatty ester;
(d) about 0.1 to about 7 wt. % of a film former;
(e) about 0.05 to about 10 wt. % of a silicone polymer; and
(f) about 0.5 to about 12 wt. % of an oil,
 wherein all weight percentages are based on the total weight of the hair cosmetic composition.

In some cases, the hair cosmetic compositions have a viscosity that decreases when the hair cosmetic composition is diluted with water at a weight ratio of about 1:0.1 to about 1:10. In at least one embodiment, the hair cosmetic composition has a viscosity that decreases when the hair cosmetic composition is diluted with water at a weight ratio of about 1:1.

In some cases, the hair styling composition may have a weight ratio of the total amount of glycol to total amount of glycerin that is about 0.1:1 to about 2.5:1. In some instances, the glycol(s) is chosen from chosen from ethylene glycol, propylene glycol, butylene glycol, hexylene glycol, pentylene glycol, diethylene glycol, caprylyl glycol, dipropylene glycol, 1,3 propanediol, ethylhexylglycerin, and a mixture thereof.

Non-limiting examples of suitable nonionic surfactants include PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil, polysorbate 85, polysorbate 60, polysorbate 80, ceterayl glucoside, polyglyceryl-3 methyglucose distearate, oleth-10, ceteth-10, ceteareth-20, or a mixture thereof.

Suitable examples of fatty esters that may be included in the hair cosmetic composition include cetyl palmitate, cetyl stearate, cetyl esters, myristyl myristate, myristyl stearate, cetyl myristate, stearyl stearate, glyceryl stearate, propylene glycol dicaprylate/dicaprate, cetearyl ethylhexanoate, isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof.

Additionally or alternatively, the hair cosmetic composition may include a quaternary ammonium polymer. In some instances, the quaternary ammonium polymer is chosen form polyquaternium 4, polyquaternium 6, polyquaternium 7, polyquaternium 10, polyquaternium 11, polyquaternium 16, polyquaternium 22, polyquaternium 28, polyquaternium 32, polyquaternium-37, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and a mixture thereof.

The "film formers" as used herein means a polymer or resin that leaves a film on the substrate to which it is applied. Examples of acceptable classes of film forming agents include acrylic polymers, vinyl pyrrolidone (VP) containing homopolymers and copolymers, polyurethanes, polyolefins, polysaccharides, polyesters and mixtures thereof. Non limiting examples of film formers include, for example, AMPHOMER LV-71 from National Starch (octylacrylamide/acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylate/ethyl acrylate/methacrylic acid), and ULTRAHOLD STRONG from BASF (acrylic acid/ethyl acrylate/t-butyl acrylamide), SALCARE SC60 from Ciba (Acrylamidopropyltrimonium Chloride/Acrylamide Copolymer), BALANCE CR from National Starch (Acrylates Copolymer), AQUAFLEX SF-40 from ISP (PVP/Vinylcaprolactam/DMAPA Acrylates Copolymers), ADVANTAGE PLUS from ISP (VA/Butyl Maleate/Isobornyl Acrylate Copolymer), MEXOMERE PW from Chimex (VA/Vinyl Butyl Benzoate/Crotonates Copolymer), GAFFIX VC-713 from ISP (Vinyl Caprolactam/VP/Dimethylaminoethyl Methacrylate Copolymer), COPOLYMER 845 from ISP (VP/Dimethylaminoethylmethacrylate Copolymer), GANEX V-516 from ISP (VP/Hexadecene Copolymer), LUVISKOL VA 64 from BASF (VP/VA Copolymer), guar hydroxypropyltrimonium chloride.

In an embodiment, the film former comprises cationic vinylpyrrolidone copolymers chosen from copolymers of vinylpyrrolidone and at least one monomer selected from the group consisting of (meth)acrylic acid; (meth)acrylates; unsaturated hydrocarbons; and vinyl monomers. In an embodiment, the film former is chosen from VP/dimethylaminoetheylamethacrylate copolymer.

In an embodiment, the silicone polymer is chosen from silicone acrylate polymers, hydroxylmethylpolysiloxane (methicone), am ine-functionalized silicones, dimethicone copolyols, polydimethylsiloxanes (dimethicones), polydiethylsiloxanes, polydimethyl siloxanes having terminal hydroxyl groups (dimethiconols), and a mixture thereof.

In an embodiment, the silicone acrylate polymers are chosen from acrylates/dimethicone copolymers, acrylates/stearyl acrylate/dimethicone acrylates copolymer, acrylates/behenyl acrylate/dimethicone acrylates copolymer), acrylates/polytrimethylsiloxymethacrylate copolymer, poly(dimethylsiloxane)-g-poly(isobutyl methacrylate), and mixtures thereof. In at least one case, the silicone polymer is acrylates/polytrimethylsiloxymethacrylate copolymer.

The oil in the hair cosmetic composition may be a plant based oil. For example, the oil may be a chosen from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, ricinus Communis seed oil, wheat germ oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof.

In at least one instance, the hair cosmetic composition comprises a fatty alcohol. For instance, the hair cosmetic composition may include cetearyl alcohol. In some embodiments, the hair cosmetic composition is an oil-in-water emulsion. In some embodiments, the hair cosmetic composition is a water-in-oil emulsion.

Additionally or alternatively, the hair cosmetic composition may include about 0.01 to about 10 wt. % of a thickening agent. Non-limiting examples of thickening agents include about 0.01 to about 10 wt. % of a thickening agent chosen from gum arabic, tragacanth gum, karaya gum, guar gum, gellan gum, tara gum, locust bean gum, tamarind gum, locust bean gum, seneca gum, sclerotium gum, gellan gum, or a mixture thereof.

According to another aspect of the disclosure, provided is a method for styling hair that includes:

(I) applying a hair cosmetic composition to hair, the hair cosmetic composition comprising:
  (a) about 4 to about 32 wt. % of two or more polyols comprising:
    (i) about 1 wt. % or more of a glycol, and
    (ii) about 2 wt. % or more of glycerin;
  (b) about 0.5 to about 10 wt. % of a nonionic surfactant;
  (c) about 2 to about 35 wt. % of a fatty ester;
  (d) about 0.1 to about 7 wt. % of a film former;
  (e) about 0.05 to about 10 wt. % of a silicone polymer; and
  (f) about 0.5 to about 12 wt. % of an oil,
    wherein all weight percentages are based on the total weight of the hair cosmetic composition; and
(II) styling or shaping the hair.

The hair cosmetic composition used in the foregoing method may include polyquaternium-37 and/or VP/dimethylaminoetheylamethacrylate copolymer, and may include a silicone polymer comprising acrylates/polytrimethylsiloxymethacrylate copolymer. The hair cosmetic composition may further comprise polyquaternium-37.

BRIEF DESCRIPTION OF THE FIGURES

Implementation of the present technology will now be described, by way of example only, with reference to the attached figures, wherein.

Figure 1:
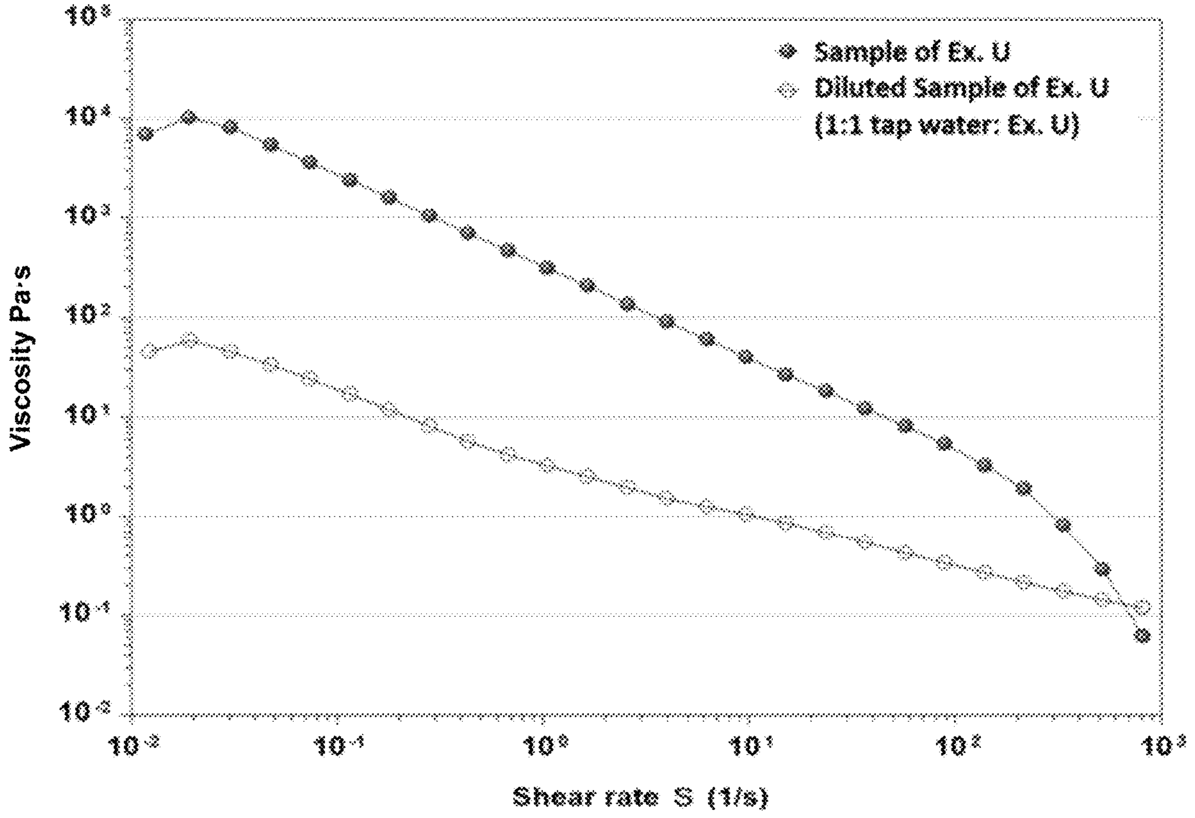
FIG. 1 is a graph of the viscosity over a range of shear stress rates for a non-limiting exemplary composition and a diluted sample of such composition.

It should be understood that the various aspects are not limited to the arrangements and instrumentality shown in the drawings.

DETAILED DESCRIPTION OF THE DISCLOSURE

Aspects of the instant disclosure relate to hair cosmetic compositions providing a unique sensorial experience. The hair cosmetic compositions are typically formulated to include specific ingredients in certain amounts and ratios, such that the hair cosmetic compositions provide a unique sensor experience. For example, certain embodiments of the disclosure provide hair cosmetic compositions in the form of a cream that transforms into an oil during application of the hair cosmetic compositions. The inventors surprisingly discovered that the transformation of the hair cosmetic compositions from a cream to an oil deposits certain ingredients to the user's hair and scalp to provide enhanced benefits, such as improved health of the scalp and hair, conditioning and moisturizing benefits.

The hair cosmetic compositions, according to an aspect of the disclosure, typically comprises:

(a) about 4 to about 32 wt. % of two or more polyols comprising:

(i) about 1 wt. % or more of a glycol, and
(ii) about 2 wt. % or more of glycerin;
(b) about 0.5 to about 10 wt. % of a nonionic surfactant;
(c) about 2 to about 35 wt. % of a fatty ester;
(d) about 0.1 to about 7 wt. % of a film former;
(e) about 0.05 to about 10 wt. % of a silicone polymer; and
(f) about 0.5 to about 12 wt. % of an oil,
wherein all weight percentages are based on the total weight of the hair cosmetic composition.

The hair cosmetic compositions may be formulated to be a leave-in composition or a rinse-off composition. As noted above, the hair cosmetic compositions preferably transform from being in the form of a cream to an oil during application of the hair cosmetic composition to the user's hair, e.g., in conjunction with extraneous water. For instance, as the user adds extraneous water to the hair cosmetic composition and applies (e.g., by rubbing, spreading and/or massaging) the hair cosmetic composition to hair, the hair cosmetic composition transforms from a cream to an oil.

In some cases, extraneous water is added to the hair cosmetic composition before during, and/or after the transformation from a cream to an oil in an amount such that the weight ratio of hair cosmetic compositions to extraneous water is about 1:0.1 to about 1:10, about 1:0.2 to about 1:10, about 1:0.3 to about 1:10, about 1:0.4 to about 1:10, about 1:0.5 to about 1:10, about 1:0.6 to about 1:10, about 1:0.7 to about 1:10, about 1:0.8 to about 1:10, about 1:0.9 to about 1:10, about 1:1 to about 1:10; about 1:0.1 to about 1:8, about 1:0.2 to about 1:8, about 1:0.3 to about 1:8, about 1:0.4 to about 1:8, about 1:0.5 to about 1:8, about 1:0.6 to about 1:8, about 1:0.7 to about 1:8, about 1:0.8 to about 1:8, about 1:0.9 to about 1:8, about 1:1 to about 1:8; about 1:0.1 to about 1:6, about 1:0.2 to about 1:6, about 1:0.3 to about 1:6, about 1:0.4 to about 1:6, about 1:0.5 to about 1:6, about 1:0.6 to about 1:6, about 1:0.7 to about 1:6, about 1:0.8 to about 1:6, about 1:0.9 to about 1:6, about 1:1 to about 1:6; about 1:0.1 to about 1:4, about 1:0.2 to about 1:4, about 1:0.3 to about 1:4, about 1:0.4 to about 1:4, about 1:0.5 to about 1:4, about 1:0.6 to about 1:4, about 1:0.7 to about 1:4, about 1:0.8 to about 1:4, about 1:0.9 to about 1:4, about 1:1 to about 1:4; about 1:0.1 to about 1:2, about 1:0.2 to about 1:2, about 1:0.3 to about 1:2, about 1:0.4 to about 1:2, about 1:0.5 to about 1:2, about 1:0.6 to about 1:2, about 1:0.7 to about 1:2, about 1:0.8 to about 1:2, about 1:0.9 to about 1:2, about 1:1 to about 1:2, or any ranges therebetween.

The viscosity of the hair cosmetic composition typically decreases upon contact with water as the hair cosmetic composition transforms from a cream to an oil. For example, the hair cosmetic composition may have a viscosity of about 10 to about 500 Pa·s, as measured at a temperature of 25° C. using a rheometer (DHR-2, TA instruments, New Castle, DE, USA) and 40 mm parallel plate geometry with shear rate at a range of 1 to 10 1/s. In some instances, the viscosity of the hair cosmetic composition, when in the form of a cream, has a viscosity of about 10 to about 500 Pa·s, about 20 to about 500 Pa·s, about 40 to about 500 Pa·s, about 60 to about 500 Pa·s, about 80 to about 500 Pa·s, about 100 to about 500 Pa·s, about 200 to about 500 Pa·s, about 10 to about 300 Pa·s, about 20 to about 300 Pa·s, about 40 to about 300 Pa·s, about 60 to about 300 Pa·s, about 80 to about 300 Pa·s, about 100 to about 300 Pa·s, about 1500 to about 300 Pa·s; about 10 to about 100 Pa·s, about 20 to about 100 Pa·s, about 40 to about 100 Pa·s, about 60 to about 100 Pa·s, about 80 to about 100 Pa·s, as measured at a temperature of 25° C. using a rheometer (DHR-2, TA instruments, New Castle, DE, USA) and 40 mm parallel plate geometry with shear rate at a range of 1 to 10 1/s. Preferably, viscosity of the hair cosmetic composition, after transforming to an oil, is less than when the hair cosmetic composition is in the form of a cream. Without being limited to any specific theory, it is believed that the shear stress associated with the application of the hair cosmetic compositions after extraneous water has been added to the hair cosmetic composition breaks the emulsion associated with the hair cosmetic composition to, at least partly, contribute to the transformation of the hair cosmetic composition from a cream to an oil. As noted above, in some instances, the transformation of the hair cosmetic composition from a cream to an oil refers to the hair cosmetic composition transforming from having rheological properties and/or a tactile feel associated with a cream to having rheological properties and/or a tactile feel associated with an oil.

The viscosity of the hair cosmetic composition, after transforming to an oil, has a viscosity of about 0.01 to about 10 Pa·s, as measured at a temperature of 25° C. using a rheometer (DHR-2, TA instruments, New Castle, DE, USA) and 40 mm parallel plate geometry with shear rate at a range of 1 to 10 1/s.

Suitable components, such as those listed below, may be included or excluded from the formulations for the cosmetic compositions depending on the specific combination of other components, the form of the cosmetic compositions, and/or the use of the formulation.

Polyols

The hair cosmetic compositions includes two or more polyols typically in an amount that ranges from about 4 to about 32 wt. %, based on the total weight of the hair cosmetic composition. For example, the total amount of polyols present in the hair cosmetic composition may be from about 4 to about 29 wt. %, about 4 to about 26 wt. %, about 4 to about 23 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %; about 4 to about 7 wt. %; about 4 to about 6 wt. %; about 5 to about 29 wt. %, about 5 to about 26 wt. %, about 5 to about 23 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %; about 6 to about 29 wt. %, about 6 to about 26 wt. %, about 6 to about 23 wt. %, about 6 to about 20 wt. %, about 6 to about 18 wt. %, about 6 to about 16 wt. %, about 6 to about 14 wt. %, about 6 to about 12 wt. %, about 6 to about 10 wt. %; about 7 to about 29 wt. %, about 7 to about 26 wt. %, about 7 to about 23 wt. %, about 7 to about 20 wt. %, about 7 to about 18 wt. %, about 7 to about 16 wt. %, about 7 to about 14 wt. %, about 7 to about 12 wt. %, about 7 to about 10 wt. %; about 8 to about 29 wt. %, about 8 to about 26 wt. %, about 8 to about 23 wt. %, about 8 to about 20 wt. %, about 8 to about 18 wt. %, about 8 to about 16 wt. %, about 8 to about 14 wt. %, about 8 to about 12 wt. %, about 8 to about 11 wt. %, including ranges and subranges therebetween, based on the total weight of the hair cosmetic composition.

The two or more polyols of the hair cosmetic compositions comprise at least one glycol and glycerin. Generally, the hair cosmetic compositions comprise about 1 wt. % or more of a glycol and about 2 wt. % or more of glycerin. The amount of glycol(s) present in the hair cosmetic composition may be about 1 to about 30 wt. %, about 1 to about 27 wt. %, about 1 to about 24 wt. %, about 1 to about 21 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 6 wt. %, about 1 to about 5 wt. %, about 1 to about 4 wt. %;

about 2 to about 30 wt. %, about 2 to about 27 wt. %, about 2 to about 24 wt. %, about 2 to about 21 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 6 wt. %, about 2 to about 5 wt. %; about 3 to about 30 wt. %, about 3 to about 27 wt. %, about 3 to about 24 wt. %, about 3 to about 21 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 6 wt. %; about 4 to about 30 wt. %, about 4 to about 27 wt. %, about 4 to about 24 wt. %, about 4 to about 21 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, about 4 to about 6 wt. %, including ranges and subranges therebetween, based on the total weight of the hair cosmetic composition.

The amount of glycerin in the hair cosmetic composition may range from about 2 to about 31 wt. %, about 2 to about 27 wt. %, about 2 to about 24 wt. %, about 2 to about 21 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 6 wt. %, about 2 to about 5 wt. %; about 3 to about 31 wt. %, about 3 to about 27 wt. %, about 3 to about 24 wt. %, about 3 to about 21 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 6 wt. %; about 4 to about 31 wt. %, about 4 to about 27 wt. %, about 4 to about 24 wt. %, about 4 to about 21 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, about 4 to about 6 wt. %; about 5 to about 31 wt. %, about 5 to about 27 wt. %, about 5 to about 24 wt. %, about 5 to about 21 wt. %, about 5 to about 18 wt. %, about 5 to about 16 wt. %, about 5 to about 14 wt. %, about 5 to about 12 wt. %, about 5 to about 10 wt. %, about 5 to about 8 wt. %; about 6 to about 31 wt. %, about 6 to about 27 wt. %, about 6 to about 24 wt. %, about 6 to about 21 wt. %, about 6 to about 18 wt. %, about 6 to about 16 wt. %, about 6 to about 14 wt. %, about 6 to about 12 wt. %, about 6 to about 10 wt. %, about 6 to about 8 wt. %; about 7 to about 31 wt. %, about 7 to about 27 wt. %, about 7 to about 24 wt. %, about 7 to about 21 wt. %, about 7 to about 18 wt. %, about 7 to about 16 wt. %, about 7 to about 14 wt. %, about 7 to about 12 wt. %, about 7 to about 10 wt. %, including ranges and subranges therebetween, based on the total weight of the hair cosmetic composition.

Preferably, the weight ratio of the total amount of glycol (s) to the total amount of glycerin is about 0.1:1 to about 2.5:1. In some instance, the hair cosmetic composition is formulated such that the weight ratio of the total amount of glycol(s) to the total amount of glycerin is about 0.1:1 to about 2.5:1, about 0.2:1 to about 2.5:1, about 0.3:1 to about 2.5:1, about 0.4:1 to about 2.5:1, about 0.5:1 to about 2.5:1, about 0.6:1 to about 2.5:1, about 0.7:1 to about 2.5:1, about 0.8:1 to about 2.5:1, about 0.9:1 to about 2.5:1, about 1:1 to about 2.5:1, about 1.1:1 to about 2.5:1, about 1.2:1 to about 2.5:1, about 1.3:1 to about 2.5:1, about 1.4:1 to about 2.5:1, about 1.5:1 to about 2.5:1, about 1.6:1 to about 2.5:1, about 1.7:1 to about 2.5:1, about 1.8:1 to about 2.5:1, about 1.9:1 to about 2.5:1, about 2:1 to about 2.5:1, about 2.1:1 to about 2.5:1; about 0.1:1 to about 2:1, about 0.2:1 to about 2:1, about 0.3:1 to about 2:1, about 0.4:1 to about 2:1, about 0.5:1 to about 2:1, about 0.6:1 to about 2:1, about 0.7:1 to about 2:1, about 0.8:1 to about 2:1, about 0.9:1 to about 2:1, about 1:1 to about 2:1, about 1.1:1 to about 2:1, about 1.2:1 to about 2:1, about 1.3:1 to about 2:1, about 1.4:1 to about 2:1, about 1.5:1 to about 2:1, about 1.6:1 to about 2:1, about 1.7:1 to about 2:1, about 1.8:1 to about 2:1, about 1.9:1 to about 2:1; about 0.1:1 to about 1.5:1, about 0.2:1 to about 1.5:1, about 0.3:1 to about 1.5:1, about 0.4:1 to about 1.5:1, about 0.5:1 to about 1.5:1, about 0.6:1 to about 1.5:1, about 0.7:1 to about 1.5:1, about 0.8:1 to about 1.5:1, about 0.9:1 to about 1.5:1, about 1:1 to about 1.5:1, about 1.1:1 to about 1.5:1, about 1.2:1 to about 1.5:1, about 1.3:1 to about 1.5:1, about 1.4:1 to about 1.5:1; about 0.1:1 to about 1:1, about 0.2:1 to about 1:1, about 0.3:1 to about 1:1, about 0.4:1 to about 1:1, about 0.5:1 to about 1:1, about 0.6:1 to about 1:1, about 0.7:1 to about 1:1, about 0.8:1 to about 1:1, about 0.9:1 to about 1:1, including ranges and subranges thereof.

The term "polyol" should be understood as meaning, within the meaning of the present disclosure, an organic molecule comprising at least two free hydroxyl groups. The polyols of the cosmetic composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Suitable polyols include glycols, such as ethylene glycol, propylene glycol, butylene glycol, hexylene glycol, diethylene glycol, and dipropylene glycol, polyethylene glycols and mixtures thereof. The polyols may be chosen from glycerin and diglycerin. In some further cases, the polyol is one or both of butylene glycol and caprylyl glycol.

Non-limiting examples of polyols that may, optionally, be included in the hair cosmetic composition include and/or may be chosen from alkanediols such as ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol or triols such as glycerin, 1,2,6-hexanotriol and trimethylolpropane, and a mixture of thereof.

Nonionic Surfactant(s)

The hair cosmetic compositions include one or more nonionic surfactant(s) in an amount typically ranging from about 0.5 to about 10 wt. %, based on the total weight of the hair cosmetic composition. The total amount of nonionic surfactants can vary but is typically about 0.5 to about 10 wt. %, about 0.5 to about 9 wt. %, about 0.5 to about 6 wt. %, about 0.5 to about 5 wt. %, about 0.5 to about 4 wt. %, about 0.5 to about 3 wt. %, about 0.5 to about 2 wt. %; about 0.75 to about 10 wt. %, about 0.75 to about 9 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 9 wt. %, about 1 to about 6 wt. %, about 1 to about 5 wt. %, about 1 to about 4 wt. %, about 1 to about 3 wt. %, about 1 to about 2 wt. %, including ranges and subranges therebetween, based on the total weight of the hair cosmetic composition.

Examples of suitable nonionic surfactants in the present disclosure are those that also function as emulsifier ("nonionic emulsifying surfactants"). The nonionic surfactant may have an HLB (hydrophilic-lipophilic balance) ranging from 1 to 7.9 or greater than or equal to 8.

"HLB" refers to the "hydrophilic-lipophilic balance" associated with nonionic surfactants or emulsifiers. In particular, "HLB" value relates to the ratio of hydrophilic groups and lipophilic groups in emulsifiers, and also relates to solubility of the emulsifiers. Lower HLB emulsifiers (such as those with HLB values ranging from 1 to 7.9) are more soluble in oils (lipophilic material) and are more appropriate for use in water-in-oil (W/O) emulsions. Higher HLB emulsifiers (such as those with HLB values higher than 8) are more soluble in water (hydrophilic material) and are more appropriate for oil-in-water (O/W) emulsions.

In an embodiment, the suitable nonionic surfactants in the present disclosure have an HLB (hydrophilic-lipophilic balance) of greater than or equal to 8.

The nonionic surfactant(s) may be chosen especially from alkyl and polyalkyl esters of poly(ethylene oxide), alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, optionally polyoxyethylenated alkyl and polyalkyl esters of glycerol, and optionally polyoxyethylenated alkyl and polyalkyl ethers of glycerol, and mixtures thereof. Preferably, the non-ionic surfactant(s) may be chosen from alkyl and polyalkyl esters of poly(ethylene oxide), alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, optionally polyoxyethylenated alkyl and polyalkyl esters of glycerol, and optionally polyoxyethylenated alkyl and polyalkyl ethers of glycerol, and mixtures thereof.

1) Alkyl and polyalkyl esters of poly(ethylene oxide) that are preferably used are those containing at least one C8-C30 alkyl radical, with a number of ethylene oxide (EO) units ranging from 2 to 200. Mention may be made, for example, of (INCI name) PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil.
2) Alkyl and polyalkyl ethers of poly(ethylene oxide) that are preferably used are those containing at least one C8-C30 alkyl radical, with a number of ethylene oxide (EO) units ranging from 3 to 200. Mention may be made, for example, of laureth-3, laureth-4, laureth-7, laureth-23, ceteth-5, ceteth-7, ceteth-15, ceteth-23, oleth-5, oleth-7, oleth-10, oleth-12, oleth-20, oleth-50, phytosterol 30 EO, steareth-6, steareth-20, steareth-21, steareth-40, steareth-100, beheneth 100, ceteareth-7, ceteareth-10, ceteareth-15, ceteareth-25, pareth-3, pareth-23, C12-15 pareth-3, C12-13 pareth-4, C12-13 pareth-23, trideceth-3, trideceth-4, trideceth-5, trideceth-6, trideceth-7 and trideceth-10, and mixtures thereof.
3) Optionally polyoxyethylenated alkyl and polyalkyl esters of sorbitan that are preferably used are those with a number of ethylene oxide (EO) units ranging from 0 to 100. Mention may be made, for example, of sorbitan laurate, sorbitan laurate 4 EO, sorbitan laurate 20 EO (polysorbate 20), sorbitan palmitate 20 EO (polysorbate 40), sorbitan stearate 20 EO (polysorbate 60), sorbitan oleate 20 EO (polysorbate 80) and sorbitan trioleate 20 EO (polysorbate 85).
4) Optionally polyoxyethylenated alkyl and polyalkyl ethers of sorbitan that are preferably used are those with a number of ethylene oxide (EO) units ranging from 0 to 100.

In an embodiment, the nonionic surfactants of the present disclosure comprise PEG-100 stearate. The nonionic surfactants may, in some instances, be chosen from PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil, polysorbate 85, polysorbate 60, polysorbate 80, ceterayl glucoside, polyglyceryl-3 methyglucose distearate, oleth-10, ceteth-10, ceteareth-20, and mixtures thereof.

Other nonionic surfactants can be additionally present in the compositions of the present disclosure. Further discussion of such nonionic surfactants is provided below.

(i) Alkanolamides

Non-limiting examples alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

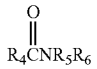

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);

$R_6$ is selected from $—CH_2OH$, $—CH_2CH_2OH$, $—CH_2CH_2CH_2OH$, $—CH_2(CHOH)_4CH_2OH$, -benzyl, and mixtures thereof;

$R_6$ is selected from —H, $—CH_3$, $—CH_2OH$, $—CH_2CH_3$, $—CH_2CH_2OH$, $—CH_2CH_2CH_2OH$, $—CH_2(CHOH)_4CH_2OH$, -benzyl, and mixtures thereof.

In some instances, the one or more of the fatty acid alkanolamides include one or more acyl glucam ides, for example, acyl glucam ides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

(ii) Alkyl Polyglucosides

Non-limiting examples of alkyl polyglucosides include those having the following formula:

$$R^1—O—(R^2O)_n—Z(x)$$

wherein $R^1$ is an alkyl group having 8-18 carbon atoms;

$R^2$ is an ethylene or propylene group;

Z is a saccharide group with 5 to 6 carbon atoms;

n is an integer from 0 to 10; and x is an integer from 1 to 5.

Useful alkyl poly glucosides include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

(iii) Miscellaneous Nonionic Surfactants

Nonionic surfactants also include, for example, alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N-($C_6$-$C_{24}$)alkylglucamine derivatives, amine oxides such as ($C_{10}$-$C_{14}$)alkylamine oxides or N-($C_{10}$-$C_{14}$)acylaminopropylmorpholine oxides; and mixtures thereof.

Such nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names:PEG-9 laurate to PEG-50 laurate); PEG-9 to PEG-50 palmitate (as the CTFA names:PEG-9 palmitate to PEG-50 palmitate); PEG-9 to PEG-50 stearate (as the CTFA names:PEG-9 stearate to PEG-50 stearate); PEG-9 to PEG-50 palmitostearate; PEG-9 to PEG-50 behenate (as the CTFA names:PEG-9 behenate to PEG-50 behenate); polyethylene glycol 100 EO monostearate (CTFA name:PEG-100 stearate); and mixtures thereof.

As glyceryl esters of fatty acids, glyceryl stearate (glyceryl mono-, di- and/or tristearate) (CTFA name:glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name:glyceryl stearate SE), can also be used.

Fatty Ester(s)

The hair cosmetic compositions include one or more fatty ester(s) in an amount that may vary, but typically ranges from about 2 to about 35 wt. %, based on the total weight of the hair cosmetic composition. For example, the fatty ester (s) may be present in the hair cosmetic composition in an amount of about 2 to about 35 wt. %, about 2 to about 30 wt. %, about 2 to about 28 wt. %, about 2 to about 26 wt. %, about 2 to about 24 wt. %, about 2 to about 22 wt. %, about 2 to about 20 wt. %, about 2 to about 18 wt. %, about 2 to about 16 wt. %, about 2 to about 14 wt. %; about 6 to about 35 wt. %, about 6 to about 30 wt. %, about 6 to about 28 wt. %, about 6 to about 26 wt. %, about 6 to about 24 wt. %, about 6 to about 22 wt. %, about 6 to about 20 wt. %, about 6 to about 18 wt. %, about 6 to about 16 wt. %, about 6 to about 14 wt. %; about 10 to about 35 wt. %, about 10 to about 30 wt. %, about 10 to about 28 wt. %, about 10 to about 26 wt. %, about 10 to about 24 wt. %, about 10 to about 22 wt. %, about 10 to about 20 wt. %, about 10 to about 18 wt. %, about 10 to about 16 wt. %, about 10 to about 14 wt. %; about 12 to about 35 wt. %, about 12 to about 30 wt. %, about 12 to about 28 wt. %, about 12 to about 26 wt. %, about 12 to about 24 wt. %, about 12 to about 22 wt. %, about 12 to about 20 wt. %, about 12 to about 18 wt. %, about 12 to about 16 wt. %; about 14 to about 35 wt. %, about 14 to about 30 wt. %, about 14 to about 28 wt. %, about 14 to about 26 wt. %, about 14 to about 24 wt. %, about 14 to about 22 wt. %, about 14 to about 20 wt. %, about 14 to about 18 wt. %; about 16 to about 35 wt. %, about 16 to about 30 wt. %, about 16 to about 28 wt. %, about 16 to about 26 wt. %, about 16 to about 24 wt. %, about 16 to about 22 wt. %, about 16 to about 20 wt. %, including ranges and subranges therebetween, based on the total weight of the hair cosmetic composition.

Suitable examples of fatty esters include cetyl palmitate, cetyl stearate, cetyl esters, myristyl myristate, myristyl stearate, cetyl myristate, stearyl stearate, glyceryl stearate, propylene glycol dicaprylate/dicaprate, cetearyl ethylhexanoate, isopropyl isostearate, n-propyl myristate, isopropyl myristate, hexyl laurate, hexadecyl isostearate, hexydecyl laurate, hexyldecyl octanoate, n-propyl palmitate, isopropyl palmitate, or mixtures thereof. In a preferred embodiment, the fatty ester is chosen from cetyl esters, glyceryl stearate, propylene glycol dicaprylate/dicaprate, isopropyl myristate, and mixtures thereof.

The fatty ester(s) may be chosen from dialkyl carbonates of formula: $R_1O(C{=}O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

Film Former(s)

The hair cosmetic composition includes one or more film-former(s) typically in an amount from about 0.1 to about 7 wt. %, based on the total weight of the hair cosmetic composition. For instance, the film formers may be present in the hair cosmetic in an amount of about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 7 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %, about 0.75 to about 1 wt. %, including ranges and subranges therebetween, based on the total weight of the hair cosmetic composition.

"Film former" as used herein means a polymer or resin that is capable, by itself or in the presence of an auxiliary film-forming agent, of forming a macroscopically continuous film that adheres leaves a film on the substrate to which it is applied, for example, after a solvent accompanying the film former has evaporated, absorbed into and/or dissipated on the substrate. Non-limiting examples of film forming polymers include, for example, PVP, PVP/VA, acrylates, polyesters, polyurethranes, polyimides, polysulfonates, gums, guars, starches, celluloses, and the like.

Further examples of film forming polymers are provided in the following list, which is not intended to be limiting: AMPHOMER LV-71 from National Starch (octylacrylamide/acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylate/ethyl acrylate/methacrylic acid), and ULTRAHOLD STRONG from BASF (acrylic acid/ethyl acrylate/t-butyl acrylamide), SALCARE SC60 from Ciba (Acrylamidopropyltrimonium Chloride/Acrylamide Copolymer), BALANCE CR from National Starch (Acrylates Copolymer), AMPHOMER 28-4961 from National Starch (Acrylates/Octylacrylamide Copolymer), TORAY SETSIL 301 from Dow Corning (Acrylates/Octylacrylamide/Diphenyl Amodimethicone Copolymer), DIAFORMER Z-632N from Clariant (Acrylates/Stearyl Acrylate/Ethylamine Oxide Methacrylate Copolymer), ULTRAHOL 8 from BASF (Acrylates/t-Butylacrylamide Copolymer), MEXOMERE PQ from Chimex (Allyl Stearate/VA Copolymer), FIXATE G-100 from Noveon (AMP-Acrylates/Allyl Methacrylate Copolymer), GANTREZ A-425 from ISP (Butyl Ester of PVM/MA Copolymer), GANEX P-904 from ISP (Butylated PVP), AMAZE from National Starch (Corn Starch Modified), MEXOMERE PL from Chimex (Diethylene Glycolamine/Epichlorohydrin/piperazine Copolymer), EASTMAN AQ POLYMER from Eastman (Diglycol/CHDM/Isophthalate/SIP Copolymer), AQUAFLEX FX-64 from ISP (Isobutylene/Ethylmaleim ide/Hydroxyethylmaleim ide Copolymer), LUVIFLEX SILK from BASF (PEG/PPG-25/25 Dimethicone/Acrylates Copolymer), AQUAFLEX XL-30 from BASF (Polyimide-1), LUVISET P.U.R from BASF (Polyurethrane-1), LUVISKOL PLUS from BASF (Polyvinylcaprolactam), AQUAFLEX SF-40 from ISP (PVP/Vinylcaprolactam/DMAPA Acrylates Copolymers), ADVANTAGE PLUS from ISP (VA/Butyl Maleate/Isobornyl Acrylate Copolymer), MEXOMERE PW from Chimex (VA/Vinyl Butyl Benzoate/Crotonates Copolymer), GAFFIX VC-713 from ISP (Vinyl Caprolactam/VP/Dimethylaminoethyl Methacrylate Copolymer), COPOLYMER 845 from ISP (VP/Dimethylaminoethylmethacrylate Copolymer), GANEX V-516 from ISP (VP/Hexadecene Copolymer), LUVISKOL VA 64 from BASF (VP/VA Copolymer).

Unneutralized or partially neutralized water-insoluble latexes include the following latexes: AMERHOLD DR-25 from Amerchol (acrylic acid/methacrylic acid/acrylates/ methacrylates), LUVIMER 36D from BASF (ethyl acrylate/t-butyl acrylate/methacrylic acid), and ACUDYNE 258 from Rohm & Haas (acrylic acid/methacrylic acid/acrylates/methacrylates/hydroxy ester acrylates).

In some instances, the film former is preferably cationic. For example, the hair cosmetic composition includes a cationic film former chosen from vp/dimethylaminoethylmethacrylate copolymer, thanaminium, N, N, N-trimethyl-2-(2-methyl-1-oxo-2-propenyl)oxy)-chloride, homopolymer, 2-(N, N-dimethylamino)ethyl 2-methyl-2-propenoate, polymer with N,N-dimethly-2-propenamide, and $C_{1-30}$-acylpoly(oxyethylene) 2-methyl-2-propenoate quaternized with diethyl sulfate, and mixtures thereof. Preferably, the film former comprises vp/dimethylaminoethylmethacrylate copolymer.

The film former may be a hydrophobic material that imparts film forming and/or waterproofing characteristics. One such agent is polyethylene, which is available from New Phase Technologies as Performalene® 400, a polyethylene having a molecular weight of 400. Another film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, and mixtures thereof. In some cases, the film former is VP/VA copolymer and/or acrylates/$C_{12}$-$C_{22}$ alkylmethacrylate copolymer, which is commercially available sold under the tradename Allianz OPT® by ISP.

Silicone Polymer(s)

The hair cosmetic compositions include one or more silicone polymer(s) in an amount that may vary, but is typically in the range of about 0.05 to about 10 wt. %, based on the total weight of hair cosmetic composition. For instance, the amount of silicone polymer present in the hair cosmetic composition may be about 0.05 to about 10 wt. %, about 0.05 to about 9 wt. %, about 0.05 to about 8 wt. %, about 0.05 to about 7 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %; about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.2 to about 10 wt. %, about 0.2 to about 9 wt. %, about 0.2 to about 8 wt. %, about 0.2 to about 7 wt. %, about 0.2 to about 6 wt. %, about 0.2 to about 5 wt. %, about 0.2 to about 4 wt. %, about 0.2 to about 3 wt. %, about 0.2 to about 2 wt. %, about 0.2 to about 1 wt. %, including ranges and subranges therebetween, based on the total weight of the hair cosmetic composition.

In some cases, the silicone polymer is chosen from acrylates/polytrimethylsiloxymethacrylate copolymer, divinyl-dimethicone/dimethicone copolymer, hydroxylmethylpolysiloxane (methicone), dimethicone, and a mixture thereof.

The silicone polymers may be chosen from amine-functionalized silicones (e.g., amodimethicone), dimethicone, bis-aminopropyl dimethicone, trimethyl silylamodimethicone, dimethicone copolyols, etc. The hair cosmetic composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicone polymers may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

In some instances, an amino-functionalized silicone polymer is selected from polymers having the following formula:

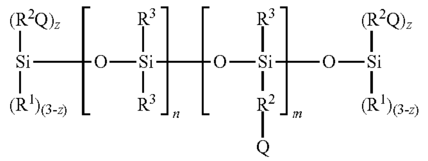

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $—NR^4_2$ and $—NR^4(CH_2)_xNR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

$R^1$ groups may include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, $—CH_2CH(CH_3)CH_2—$ and $—CH_2CH_2CH(CH_3)CH_2—$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicone polymer has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. In some instance, n+m is 50 to 750. In further instances, n+m is 50 to 500. In yet further instances, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

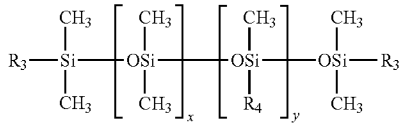

wherein $R_3$ is hydroxyl or $OR_5$, $R_5$ is a $C_1$ to $C_4$ alkyl group, $R_4$ is a group with structure according to the following formula:

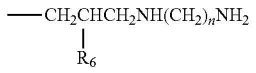

$R_6$ is a $C_1$ to $C_4$ alkyl, n is a 1 to 4, x is the same as "n" described above, and y is the same as "m" described above.

The silicone may be a polysiloxane corresponding to the following formula:

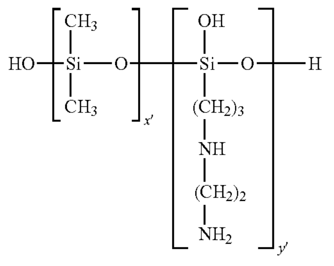

in which x' and y' are integers such that the weight-average molecular weight (Mw) is comprised between about 5000 and 500 000.

The silicone polymers may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

In some cases, the silicone polymers, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

The silicone polymers may be chosen from silicone acrylate copolymers. Suitable silicone acrylate copolymers include polymers comprising a siloxane group and a hydrocarbon group. For example, suitable polymers include polymers comprising a hydrocarbon backbone such as, for example, a backbone chosen from vinyl polymers, methacrylic polymers, and/or acrylic polymers and at least one chain chosen from pendant siloxane groups, and polymers comprising a backbone of siloxane groups and at least one pendant hydrocarbon chain such as, for example, a pendant vinyl, methacrylic and/or acrylic groups.

The at least one silicone acrylate copolymer can be chosen from silicone/(meth)acrylate copolymers, such as those as described in U.S. Pat. Nos. 5,061,481, 5,219,560, and 5,262,087, and U.S. patent application 2012/0301415, the entire contents of all of which are hereby incorporated by reference.

The at least one silicone acrylate copolymer may be selected from polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (INCI name: isododecane (and) acrylate/dimethicone copolymer), KP-561 (acrylates/stearyl acrylate/dimethicone acrylates copolymer), KP-562 (acrylates/behenyl acrylate/dimethicone acrylates copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer), FA 4002 ID SILICONE ACRYLATE (isododecane (and) acrylates/polytrimethylsiloxymethacrylate Copolymer), and FA 4004 ID SILICONE ACRYLATE (isododecane (and) acrylates/polytrimethylsiloxymethacrylate Copolymer), and mixtures thereof.

Further non-limiting examples of such polymers and their synthesis are disclosed, for example, in U.S. Pat. Nos. 4,972,037, 5,061,481, 5,209,924, 5,849,275, and 6,033,650, and PCT applications WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other useful polymers include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

Oil(s)

The hair cosmetic compositions include one or more oils typically in the amount of about 0.5 to about 12 wt. %, based on the total weight of the hair cosmetic composition. In some instances, the oils are in an amount ranging from about 0.5 to about 12 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %; about 1 to about 12 wt. %, about 1 to about 10 wt. %, about 1 to about 8 wt. %, about 1 to about 6 wt. %, about 1 to about 5 wt. %, about 1 to about 4 wt. %, about 1 to about 3 wt. %; about 1.5 to about 12 wt. %, about 1.5 to about 10 wt. %, about 1.5 to about 8 wt. %, about 1.5 to about 6 wt. %, about 1.5 to about 5 wt. %, about 1.5 to about 4 wt. %, about 1.5 to about 3 wt. %; about 2 to about 12 wt. %, about 2 to about 10 wt. %, about 2 to about 8 wt. %, about 2 to about 6 wt. %, about 2 to about 5 wt. %, about 2 to about 4 wt. %; about 3 to about 12 wt. %, about 3 to about 10 wt. %, about 3 to about 8 wt. %, about 3 to about 6 wt. %, about 3 to about 5 wt. %; about 4 to about 12 wt. %, about 4 to about 10 wt. %, about 4 to about 8 wt. %, about 4 to about 6 wt. %; about 5 to about 12 wt. %, about 5 to about 10 wt. %, about 5 to about 8 wt. %, about 5 to about 7 wt. %; about 6 to about 12 wt. %, about 6 to about 10 wt. %, about 6 to about 8 wt. %; about 7 to about 12 wt. %, about 7 to about 10 wt. %, about 7 to about 9 wt. %; about 8 to about 12 wt. %, about 8 to about 12 wt. %, about 8 to about 10 wt. %; about 9 to about 12 wt. %, about 9 to about 11 wt. %, including ranges and subranges therebetween, based on the total weight of the hair cosmetic composition.

The oil component of the NLCs is typically has melting temperature of less than 45° C., a molecular weight of at least 190, and a solubility in water of no greater than 1 part in 99 parts of water.

Non-limiting examples of include, but are not limited to, natural oils, such as coconut oil; hydrocarbons, such as mineral oil and hydrogenated polyisobutene; esters, such as $C_{12}$-$C_{15}$ alkyl benzoate; diesters, such as propylene dipelarganate; and triesters, such as glyceryl trioctanoate. Further examples of oils that may, optionally, be included in the hair cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Additionally or alternatively, the oil may be selected from plant based and/or vegetable oils. Non-limiting examples of plant-based or vegetable oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, ricinus Communis (castor) seed oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

In at least one preferred embodiment, the oil comprises a plant based oil, such as ricinus Communis (castor) seed oil and a hydrocarbon oil or (iso)paraffin such as isododecane or isohexadecane or mineral oil. In another preferred embodiment, the oil comprises a plant based oil, such as ricinus Communis (castor) seed oil, and a non-plant based oil, such isododecane or isohexadecane.

Quaternary Ammonium Polymer(s)

The hair cosmetic composition may include one or more quaternary ammonium polymer(s). The amount of quaternary ammonium polymers, if present in the hair cosmetic composition, is typically in a range of about 0.1 to about 7 wt. %, based on the total weight of the hair cosmetic composition. For instance, the quaternary ammonium polymers may be present in the hair cosmetic composition in an amount of about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 7 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.6 to about 7 wt. %; about 0.6 to about 5 wt. %; about 0.6 to about 3 wt. %; about 0.6 to about 2 wt. %; about 0.6 to about 1 wt. %; about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %, about 0.75 to about 1 wt. %, including ranges and subranges therebetween, based on the total weight of the hair cosmetic composition.

The quaternary ammonium polymers can comprise mixtures of monomer units derived from amine- and/or quaternary ammonium-substituted monomer and/or compatible spacer monomers. Suitable quaternary ammonium polymers include, for example: copolymers of 1-vinyl-2-pyrrolidine and 1-vinyl-3-methyl-imidazolium salt (e.g., chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other quaternary ammonium polymers that may be used include polysaccharide polymers, such as cationic guar, cationic cellulose derivatives and cationic starch derivatives. Cationic guar (INCI name: Guar Hydroxylpropyltrimonium Chloride) is available under the tradename of JAGUAR C 13S from Rhodia or N-Hance from Ashland. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200.

The hair cosmetic composition may include quaternary ammonium polymers chosen from polyquaterniums. For example, the hair cosmetic composition may include Polyquaternium-1 (ethanol, 2,2',2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylam ide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In at least one preferable embodiment, the quaternary ammonium polymers may be chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-37, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, or a mixture thereof. In another preferable embodiment, the hair cosmetic composition comprises polyquaternium-37.

Fatty Alcohol(s)

The hair cosmetic compositions may optionally include one or more fatty alcohol. The fatty alcohols, if present, may be in the hair cosmetic composition in an amount of about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %; about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; about 2 to about 8 wt. %, about 2 to about 7 wt. %, about 2 to about 6 wt. %, about 2 to about 5 wt. %, about 2 to about 4 wt. %; about 2.5 to about 8 wt. %, about 2.5 to about 7 wt. %, about 2.5 to about 6 wt. %, about 2.5 to about 5 wt. %, about 2.5 to about 4 wt. %; about 3 to about 8 wt. %, about 3 to about 7 wt. %, about 3 to about 6 wt. %, about 3 to about 5 wt. %, including ranges and subranges therebetween, based on the total weight of the hair cosmetic compositions.

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Thickening Agent(s)

The hair cosmetic compositions described herein may, optionally, include a thickening agent. The amount of thickening agents can vary but is typically from about 0.01 to about 10 wt. %, based on the total weight of the hair cosmetic composition. In some instances, the amount of thickening agents present in the hair cosmetic compositions is about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.05 to about 10 wt. %, about 0.05 to about 8 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %; about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %, including all ranges and sub-ranges therebetween, based on the total weight of the hair cosmetic composition.

The thickening agent(s) may be chosen from guar gum, biosaccharide gum, cellulose, acacia seneca gum, sclerotium gum, agarose, pechtin, gellan gum, hyaluronic acid. In some cases, the hair cosmetic composition may be free of or substantially free of xanthan gum.

Additionally or alternatively, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. Further examples of thickening agents, which may be suitable, can be found in U.S. patent application Ser. No. 16/731,654, which is incorporated herein, in its entirety for all purposes.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the cosmetic compositions of the instant disclosure. Thickening agents may be referred to as "thickeners" or "viscosity modifying agents." Thickening agents are typically included to increase the viscosity of the cosmetic compositions. Nonetheless, in some instances, certain thickening agents provide additional, surprising benefits to the hair cosmetic compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, $C_{8-24}$ hydroxyl substituted aliphatic acid, $C_{8-24}$ conjugated aliphatic acid, sugar fatty esters, polyglyceryl esters, and a mixture thereof. Particular types of thickening agents that may be mentioned include the following:

(I) Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid cross-linked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

(ii) Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

(iii) Polyvinylpyrrolidone (PVP) and Co-Polymers:

Non-limiting examples include Polyvinylpyrrolidone (PVP), Polyvinylpyrrolidone(PVP)/vinyl acetate copolymer (PVP/VA copolymer), polyvinylpyrrolidone (PVP)/eicosene copolymer, PVP/hexadecene copolymer, etc.

Commercially available polyvinylpyrrolidone includes LUVISKOL $K_{30}$, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI:VP/Methacrylamide/Vinyl Imidazole Copolymer) is commercially available as LUVISET from BASF. In some instances, PVP and PVP/VA copolymer are preferred.

(iv) Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

(v) Polyglyceryl Esters:

Non-limiting polyglycerol esters of fatty acids (polyglyceryl esters) include those of the following formula:

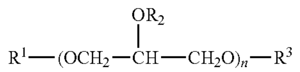

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

(vi) Gums:

Non-limiting examples of gums include gum arabic, tragacanth gum, karaya gum, guar gum, gellan gum, tara gum, locust bean gum, tamarind gum, locust bean gum, Seneca gum, sclerotium gum, gellan gum, etc.

pH Adjuster(s)

The hair cosmetic composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The hair cosmetic composition may include one or more bases, such as sodium hydroxide, potassium hydroxide and the like, to increase the pH of the hair cosmetic composition. Additional or alternative acids and bases that are suitable for adjusting the pH of the hair cosmetic composition are readily known to one of ordinary skill in the art.

The amount of the pH adjuster in the hair cosmetic composition may be based on the desired pH of the final hair cosmetic composition and/or product. For example, the hair cosmetic composition may have an amount of pH adjusters such that the pH of the composition is about 3 to about 7, preferably about 3.5 to about 6.5, preferably about 3.5 to about 6, or preferably about 3.5 to about 5.5, including ranges and sub-ranges therebetween.

The amount of the pH adjuster in the hair cosmetic composition may be based on the desired pH of the final hair cosmetic composition and/or product. For example, the total amount of the pH adjuster may range from about 0.05 to about 20 wt. %, based on the total weight of the hair cosmetic composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the hair cosmetic composition.

Chelatinq Agent(s)

The hair cosmetic composition may, optionally, include chelating agents. The amount of chelating agent present in the hair cosmetic composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the hair cosmetic composition.

Non-limiting examples of chemical chelating agents include aminotrimethyl phosphonic acid, ß-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium am inotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylamine oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate.

In at least one instance, the chelating agent is trisodium ethylenediamine disuccinate.

Preservative(s)

Preservatives may be included in the hair cosmetic composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the hair cosmetic composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Water

The hair cosmetic composition typically includes 40 wt. % or more of water. For example, the amount of water present in the hair cosmetic composition prior to combination with extraneous water may be about 40 wt. % or more, 45 wt. % or more, 50 wt. % or more, about 55 wt. % or more, about 60 wt. % or more, about 65 wt. % or more, about 70 wt. % or more, about 75 wt. % or more, about 80 wt. % or more, about 85 wt. % or more, or about 90 wt. % or more, based on the total weight of the hair cosmetic composition. Additionally or alternatively, the hair cosmetic compositions may have about 95 wt. % or less, about 90 wt. % or less, about 85 wt. % or less, about 80 wt. % or less, about 75 wt. % or less, about 70 wt. % or less, about 65 wt. % or less, about 60 wt. % or less, about 55 wt. % or less, or about 50 wt. % or less, based on the total weight of the hair cosmetic composition. In some embodiments, the hair cosmetic compositions have an amount of water that is about 40 to about 90 wt. %, about 45 to about 80 wt. %, about 48 to about 75 wt. %, including ranges and subranges therebetween, based on the total weight of the hair cosmetic composition.

Method of Use

The methods of styling hair using the hair cosmetic compositions disclosed herein typically comprise:

(I) applying a hair cosmetic composition to hair, the hair cosmetic composition comprising:
  (a) about 4 to about 32 wt. % of two or more polyols comprising:
    (i) about 1 wt. % or more of a glycol, and
    (ii) about 2 wt. % or more of glycerin;
  (b) about 0.5 to about 10 wt. % of a nonionic surfactant;
  (c) about 2 to about 35 wt. % of a fatty ester;
  (d) about 0.1 to about 7 wt. % of a film former;
  (e) about 0.05 to about 10 wt. % of a silicone polymer;
  (f) about 0.5 to about 12 wt. % of an oil; and
  (g) water,
  wherein all weight percentages are based on the total weight of the hair cosmetic composition; and
(II) styling or shaping the hair.

The hair cosmetic composition may be applied to and dispersed throughout the hair by hand, using a comb/brush, or using any other suitable means. Extraneous water may be combined with the hair cosmetic composition before, during, or after application of the hair cosmetic composition to the hair. In certain instances, as the hair cosmetic composition becomes mixed or placed in contact with extraneous water, the hair cosmetic composition transform from a cream to an oil. In certain other instances, as the hair cosmetic composition is sheared or rubbed between dry or wet hand or applied directly to hair by rubbing or shearing or spreading or massaging onto the hair and/or scalp, the hair cosmetic composition transforms from a cream to an oil. As noted above, in some instances, the transformation of the hair cosmetic composition from a cream to an oil refers to the hair cosmetic composition transforming from having rheological properties and/or a tactile feel and/or visual appearance associated with a cream to having rheological properties and/or a tactile feel and/or visual appearance associated with an oil.

The extraneous water may be combined with the hair cosmetic composition directly from a source, such as a shower, bath, sink, hose, and/or the like, or indirectly from a source, such as from wet or damp hands, wet or damp skin, wet or damp hair, and/or the like. The user may then physically manipulate the applied hair cosmetic composition (for example, by rubbing the hands together or rubbing the composition against another part of the body such as the head, hair, etc.). In some instances, the transformation from a cream to an oil occurs automatically without the need for mixing and/or shear. In other words, the hair cosmetic composition becomes sufficiently combined with extraneous water by simply coming into contact with the extraneous water. In some instances, however, a minimal amount of mixing and/or shear may be needed, and may be encouraged. Additionally, the hair may be styled using any suitable means to obtain desirable hairstyles.

Method of Manufacture

The methods for producing a hair cosmetic composition as disclosed herein typically comprise:

(I) mixing a nonionic surfactant (emulsifying), oil, fatty esters, thickening agents, and water, in any order;
(II) mixing in the polyols, film formers, and silicone polymers, in any order, into the mixture of (I),
wherein the hair cosmetic composition comprises:
(a) about 4 to about 32 wt. % of two or more polyols comprising:
  (i) about 1 wt. % or more of a glycol, and
  (ii) about 2 wt. % or more of glycerin;

(b) about 0.5 to about 10 wt. % of a nonionic surfactant;
(c) about 2 to about 35 wt. % of a fatty ester;
(d) about 0.1 to about 7 wt. % of a film former;
(e) about 0.05 to about 10 wt. % of a silicone polymer;
(f) about 0.5 to about 12 wt. % of an oil;
(g) water, wherein all weight percentages are based on the total weight of the hair cosmetic composition.

The methods for producing a hair cosmetic composition as described herein may utilize any suitable equipment, such as standard equipment for mixing, homogenizing, heating, storing, cooling, and the like, used for producing cosmetic products. The present disclosure also envisages kits and/or prepackaged materials suitable for consumer use containing one or more compositions according to the description herein. The packaging and application device for any subject of the invention may be chosen and manufactured by persons skilled in the art on the basis of their general knowledge, and adapted according to the nature of the composition to be packaged. For example, the type of device to be used can be in particular linked to the consistency of the composition, in particular to its viscosity; it can also depend on the nature of the constituents present in the composition, such as the presence of volatile compounds.

Embodiments of the Disclosure

In accordance with at least one embodiment of the disclosure, provided is a hair cosmetic composition including about 4 to about 32 wt. %, preferably about 4 to about 26 wt. %, more preferably about 4 to about 20 wt. %, of two or more polyols comprising:

(i) about 1 wt. % or more, preferably about 1 to about 20 wt. %, more preferably about 1 to about 10 wt. %, of a glycol chosen from ethylene glycol, propylene glycol, butylene glycol, hexylene glycol, pentylene glycol, diethylene glycol, caprylyl glycol, dipropylene glycol, 1,3 propanediol, ethylhexylglycerin, and a mixture thereof, and (ii) about 2 wt. % or more, preferably about 2 to about 20 wt. %, more preferably about 2 to about 10 wt. %, of glycerin;

about 0.5 to about 10 wt. %, preferably about 0.5 to about 9 wt. %, more preferably about 0.5 to about 6 wt. %, of a nonionic surfactant, wherein the nonionic surfactant is chosen from PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil, polysorbate 85, polysorbate 60, polysorbate 80, ceteryl glucoside, polyglyceryl-3 methyglucose distearate, oleth-10, ceteth-10, ceteareth-20, and a mixture thereof;

about 2 to about 35 wt. %, preferably about 6 to about 35 wt. %, more preferably about 10 to about 30 wt. %, of a fatty ester, such as those chosen from cetyl palmitate, cetyl stearate, cetyl esters, myristyl myristate, myristyl stearate, cetyl myristate, stearyl stearate, glyceryl stearate, propylene glycol dicaprylate/dicaprate, cetearyl ethylhexanoate, isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof;

about 0.1 to about 7 wt. %, preferably about 0.1 to about 6 wt. %, more preferably about 0.1 to about 5 wt. %, of a film former, the film former preferably being a cationic vinylpyrrolidone copolymers chosen from copolymers of vinylpyrrolidone and at least one monomer selected from the group consisting of (meth)acrylic acid; (meth)acrylates; unsaturated hydrocarbons; and vinyl monomers;

about 0.05 to about 10 wt. %, preferably about 0.05 to about 8 wt. %, more preferably about 0.05 to about 6 wt. %, of a silicone polymer, such as those chosen from silicone acrylate polymers, hydroxylmethylpolysiloxane (methicone), amine-functionalized silicones, dimethicone copolyols, polydimethylsiloxanes (dimethicones), polydiethylsiloxanes, polydimethyl siloxanes having terminal hydroxyl groups (dimethiconols), and a mixture thereof, preferably chosen from silicone acrylate polymers such as acrylates/dimethicone copolymers, acrylates/stearyl acrylate/dimethicone acrylates copolymer, acrylates/behenyl acrylate/dimethicone acrylates copolymer), acrylates/polytrimethylsiloxymethacrylate copolymer, poly(dimethylsiloxane)-g-poly(isobutyl methacrylate), and mixtures thereof;

about 0.5 to about 12 wt. %, preferably about 0.5 to about 10 wt. %, more preferably about 0.5 to about 8 wt. %, of an oil, e.g., a plant based oil chosen from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, ricinus Communis seed oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof;

water, preferably in an amount of about 40 wt. % or more of water, or more preferably in an amount of about 40 to about 90 wt. % of water, wherein all weight percentages are based on the total weight of the hair cosmetic composition.

According to further embodiments of the disclosure, provided is a method of styling hair comprising:

(I) applying a hair cosmetic composition to hair, the hair cosmetic composition comprising:

about 4 to about 32 wt. %, preferably about 4 to about 26 wt. %, more preferably about 4 to about 20 wt. %, of two or more polyols comprising:

(i) about 1 wt. % or more, preferably about 1 to about 20 wt. %, more preferably about 1 to about 10 wt. %, of a glycol chosen from ethylene glycol, propylene glycol, butylene glycol, hexylene glycol, pentylene glycol, diethylene glycol, caprylyl glycol, dipropylene glycol, 1,3 propanediol, ethylhexylglycerin, and a mixture thereof, and (ii) about 2 wt. % or more, preferably about 2 to about 20 wt. %, more preferably about 2 to about 10 wt. %, of glycerin;

about 0.5 to about 10 wt. %, preferably about 0.5 to about 9 wt. %, more preferably about 0.5 to about 6 wt. %, of a nonionic surfactant, wherein the nonionic surfactant is chosen from the non-ionic surfactant is chosen from PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil, polysorbate 85, polysorbate 60, polysorbate 80, ceteryl glucoside, polyglyceryl-3 methyglucose distearate, oleth-10, ceteth-10, ceteareth-20, and a mixture thereof;

about 2 to about 35 wt. %, preferably about 6 to about 35 wt. %, more preferably about 10 to about 30 wt. %, of a fatty ester, such as those chosen from cetyl palmitate, cetyl stearate, cetyl esters, myristyl myristate, myristyl stearate, cetyl myristate, stearyl stearate, glyceryl stearate, propylene glycol dicaprylate/dicaprate, cetearyl ethylhexanoate, isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof;

about 0.1 to about 7 wt. %, preferably about 0.1 to about 6 wt. %, more preferably about 0.1 to about 5 wt. %, of a film former, the film former preferably being a cationic vinylpyrrolidone copolymers chosen from copolymers of vinylpyrrolidone and at least one monomer selected from the group consisting of (meth)acrylic acid; (meth)acrylates; unsaturated hydrocarbons; and vinyl monomers;

about 0.05 to about 10 wt. %, preferably about 0.05 to about 8 wt. %, more preferably about 0.05 to about 6 wt. %, of a silicone polymer, such as those chosen from silicone acrylate polymers, hydroxylmethylpolysiloxane (methicone), am ine-functionalized silicones, dimethicone copolyols, polydimethylsiloxanes (dimethicones), polydiethylsiloxanes, polydimethyl siloxanes having terminal hydroxyl groups (dimethiconols), and a mixture thereof, preferably chosen from silicone acrylate polymers such as acrylates/dimethicone copolymers, acrylates/stearyl acrylate/dimethicone acrylates copolymer, acrylates/behenyl acrylate/dimethicone acrylates copolymer), acrylates/polytrimethylsiloxymethacrylate copolymer, poly(dimethylsiloxane)-g-poly (isobutyl methacrylate), and mixtures thereof.

about 0.5 to about 12 wt. %, preferably about 0.5 to about 10 wt. %, more preferably about 0.5 to about 8 wt. %, of an oil, e.g., a plant based oil chosen from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, ricinus Communis seed oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof; and water, preferably in an amount of about 40 wt. % or more of water, or more preferably in an amount of about 40 to about 90 wt. % of water, wherein all weight percentages are based on the total weight of the hair cosmetic composition, (II) styling the hair.

In yet other embodiments of the disclosure, provided is a method for producing a hair cosmetic composition comprising:

(I) mixing a nonionic surfactant (emulsifying), oil, fatty esters, thickening agents, and water, in any order;

(II) mixing in the polyols, film formers, and silicone polymers, in any order, into the mixture of (I), wherein the hair cosmetic composition comprises:

about 4 to about 32 wt. %, preferably about 4 to about 26 wt. %, more preferably about 4 to about 20 wt. %, of two or more polyols comprising:

(i) about 1 wt. % or more, preferably about 1 to about 20 wt. %, more preferably about 1 to about 10 wt. %, of a glycol chosen from ethylene glycol, propylene glycol, butylene glycol, hexylene glycol, pentylene glycol, diethylene glycol, caprylyl glycol, dipropylene glycol, 1,3 propanediol, ethylhexylglycerin, and a mixture thereof, and (ii) about 2 wt. % or more, preferably about 2 to about 20 wt. %, more preferably about 2 to about 10 wt. %, of glycerin;

about 0.5 to about 10 wt. %, preferably about 0.5 to about 9 wt. %, more preferably about 0.5 to about 6 wt. %, of a nonionic surfactant, wherein the nonionic surfactant is chosen from PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil, polysorbate 85, polysorbate 60, polysorbate 80, ceterayl glucoside, polyglyceryl-3 methyglucose distearate, oleth-10, ceteth-10, ceteareth-20, and a mixture thereof;

about 2 to about 35 wt. %, preferably about 6 to about 35 wt. %, more preferably about 10 to about 30 wt. %, of a fatty ester, such as those chosen from cetyl palmitate, cetyl stearate, cetyl esters, myristyl myristate, myristyl stearate, cetyl myristate, stearyl stearate, glyceryl stearate, propylene glycol dicaprylate/dicaprate, cetearyl ethylhexanoate, isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof;

about 0.1 to about 7 wt. %, preferably about 0.1 to about 6 wt. %, more preferably about 0.1 to about 5 wt. %, of a film former, the film former preferably being chosen from a cationic vinylpyrrolidone copolymers chosen from copolymers of vinylpyrrolidone and at least one monomer selected from the group consisting of (meth)acrylic acid; (meth)acrylates; unsaturated hydrocarbons; and vinyl monomers;

about 0.05 to about 10 wt. %, preferably about 0.05 to about 8 wt. %, more preferably about 0.05 to about 6 wt. %, of a silicone polymer, such as those chosen from silicone acrylate polymers, hydroxylmethylpolysiloxane (methicone), am ine-functionalized silicones, dimethicone copolyols, polydimethylsiloxanes (dimethicones), polydiethylsiloxanes, polydimethyl siloxanes having terminal hydroxyl groups (dimethiconols), and a mixture thereof, preferably chosen from silicone acrylate polymers such as acrylates/dimethicone copolymers, acrylates/stearyl acrylate/dimethicone acrylates copolymer, acrylates/behenyl acrylate/dimethicone acrylates copolymer), acrylates/polytrimethylsiloxymethacrylate copolymer, poly(dimethylsiloxane)-g-poly (isobutyl methacrylate), and mixtures thereof.

about 0.5 to about 12 wt. %, preferably about 0.5 to about 10 wt. %, more preferably about 0.5 to about 8 wt. %, of an oil, e.g., a plant based oil chosen from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, ricinus communis seed oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof; and water, preferably in an amount of about 40 wt. % or more of water, or more preferably in an amount of about 40 to about 90 wt. % of water, wherein all weight percentages are based on the total weight of the hair cosmetic composition.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty alcohol may be characterized as both a nonionic surfactant and a fatty compound. If a particular composition includes both a nonionic surfactant and a fatty compound, a single fatty alcohol will serve as only the nonionic surfactant or as only the fatty compound (the single fatty alcohol does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

Example 1
(Exemplary Compositions)

| | INCI US Name | Ex. A | Ex. B | Ex. C | Ex. D | Ex. E | Ex. F | Ex. G |
|---|---|---|---|---|---|---|---|---|
| (a) Polyols | GLYCERIN | 2 | 2 | 2 | 2 | 7 | 7 | 7 |
| | BUTYLENE GLYCOL | 3 | 2 | 3 | 3 | 3 | 3 | 3 |
| | CAPRYLYL GLYCOL | 0.01 | 0.01 | 0.01 | 0.41 | 0.01 | 0.01 | 0.01 |

-continued

Example 1
(Exemplary Compositions)

| | | | | | | | | | |
|---|---|---|---|---|---|---|---|---|---|
| | Weight ratio of glycol to glycerin | | 1.5 | 1 | 1.5 | 1.5 | 0.43 | 0.43 | 0.43 |
| | Total Amount of Polyols | | 5 | 4 | 5 | 5.4 | 10 | 10 | 10 |
| (b) | Nonionic surfactants | SORBITAN OLEATE, PEG-100 STEARATE, and PPG-1 TRIDECETH-6 | 1.1 | 1.6 | 1.1 | 1.7 | 1.1 | 1.1 | 1.1 |
| (c) | Fatty Esters | CETYL ESTERS, ISOPROPYL MYRISTATE, GLYCERYL STEARATE, and PROPYLENE GLYCOL DICAPRYLATE/DICAPRATE | 16.5 | 17 | 16.5 | 22.2 | 16.5 | 13 | 13 |
| | Quaternary ammonium polymers | POLYQUATERNIUM-37 | 0.7 | 0.7 | 0.7 | 1 | 0.7 | 0.7 | 0.7 |
| (d) | Film former | VP/ DIMETHYLAMINOETHYLMETHACRYLATE COPOLYMER[1] | 0.6 | 0.6 | 0.6 | 0.6 | 0.6 | 0.6 | 0.6 |
| (e) | Silicone Polymer | ACRYLATES/ POLYTRIMETHYLSILOXYMETHACRYLATE COPOLYMER[2] | 0.12 | 0.16 | 0.12 | 0.12 | 0.12 | 0.12 | 0.12 |
| (f) | Oil | ISODODECANE, and *RICINUS COMMUNIS* (CASTOR) SEED OIL | 1.7 | 2.2 | 1.7 | 3.2 | 1.7 | 1.7 | 1.7 |
| (h) | Fatty Alcohol | CETEARYL ALCOHOL | 1.5 | 1.5 | 1.5 | 1.5 | 1.5 | 1.5 | 3 |
| (i) | Thickening Agent | GELLAN GUM | 0.1 | | 0.1 | | | | |
| | Preservatives | PHENOXYETHANOL, and/or TOCOPHEROL, and/or ETHYLHEXYLGLYCERIN, and/or BENZOIC ACID | 0.9 | 0.9 | 1 | 0.9 | 0.9 | 0.9 | 0.9 |
| | Fragrance | FRAGRANCE | 0.9 | | | | | | 1 |
| (g) | Water | Water | QS to 100 | QS to 100 | QS to 100 | QS to 100 | QS to 100 | QS to 100 | QS to 100 |

| | | INCI US Name | Ex. H | Ex. I | Ex. J | Ex. K | Ex. L | Ex. M |
|---|---|---|---|---|---|---|---|---|
| (a) | Polyols | GLYCERIN | 7 | 2 | 2 | 5 | 2 | 2 |
| | | BUTYLENE GLYCOL | 3 | 3 | 3 | 3 | 3 | 3 |
| | | CAPRYLYL GLYCOL | 0.01 | 0.41 | 0.01 | 0.01 | 0.41 | 0.41 |
| | Weight ratio of glycols to glycerin | | 0.43 | 1.5 | 1.5 | 0.6 | 1.5 | 1.5 |
| | Total Amount of Polyols | | 10 | 5.4 | 5.4 | 8 | 5.4 | 5.4 |
| (b) | Nonionic surfactants | SORBITAN OLEATE, PEG-100 STEARATE, and PPG-1 TRIDECETH-6 | 1.1 | 1.7 | 1.7 | 1.6 | 1.7 | 1.7 |
| (c) | Fatty Esters | CETYL ESTERS, ISOPROPYL MYRISTATE, GLYCERYL STEARATE, and PROPYLENE GLYCOL DICAPRYLATE/DICAPRATE | 13 | 22.2 | 20.2 | 18 | 22.2 | 27.2 |
| | Quaternary ammonium polymer | POLYQUATERNIUM-37 | 0.7 | 1 | 1 | 0.7 | 1 | 1 |
| (d) | Film former | VP/ DIMETHYLAMINOETHYLMETHACRYLATE COPOLYMER[1] | 0.6 | 0.6 | 0.6 | 0.6 | 0.6 | 0.6 |
| (e) | Silicone Polymer | ACRYLATES/ POLYTRIMETHYLSILOXYMETHACRYLATE COPOLYMER[2] | 0.12 | 0.12 | 0.12 | 0.12 | 0.12 | 0.12 |
| (f) | Oil | ISODODECANE and *RICINUS COMMUNIS* (CASTOR) SEED OIL | 1.7 | 3.2 | 3.2 | 3.2 | 8.2 | 3.2 |
| (h) | Fatty Alcohol | CETEARYL ALCOHOL | 3 | 0.5 | 1 | 3 | 1.5 | 1.5 |
| | Preservatives | PHENOXYETHANOL, TOCOPHEROL, ETHYLHEXYLGLYCERIN, and BENZOIC ACID | 0.9 | 0.9 | 1.1 | 1.1 | 0.9 | 0.9 |
| | Fragrance | FRAGRANCE | 0.9 | | | | | |
| (g) | Water | Water | QS to 100 | QS to 100 | QS to 100 | QS to 100 | QS to 100 | QS to 100 |

| | | INCI US Name | Ex. N | Ex. O | Ex. P | Ex. Q | Ex. R | Ex. S | Ex. T | Ex. U |
|---|---|---|---|---|---|---|---|---|---|---|
| (a) | Polyols | GLYCERIN | 2 | 2 | 2 | 2 | 2 | 7 | 2 | 2 |
| | | BUTYLENE GLYCOL and | 3 | 3 | 3 | 3 | 3 | 1 | 3 | 3 |
| | | CAPRYLYL GLYCOL | 0.41 | 0.41 | 0.41 | 0.41 | 0.41 | 0.01 | 0.01 | 0.01 |
| | Weight ratio of glycols to glycerin | | 1.5 | 1.5 | 1.5 | 1.5 | 1.5 | 0.14 | 1.5 | 1.5 |
| | Total Amount of Polyols | | 5.4 | 5.4 | 5.4 | 5.4 | 5.4 | 8 | 6.5 | 6.5 |

-continued

Example 1
(Exemplary Compositions)

| | | | | | | | | | | |
|---|---|---|---|---|---|---|---|---|---|---|
| (b) | Nonionic surfactants | SORBITAN OLEATE, PEG-100 STEARATE, and PPG-1 TRIDECETH-6 | 1.7 | 1.7 | 1.7 | 1.7 | 1.7 | 1.1 | 1.1 | 1.1 |
| (c) | Fatty Esters | CETYL ESTERS, ISOPROPYL MYRISTATE, GLYCERYL STEARATE, and PROPYLENE GLYCOL DICAPRYLATE/DICAPRATE | 27.2 | 32.2 | 20.1 | 18.6 | 23.5 | 11.5 | 16.5 | 16.5 |
| | Quaternary ammonium polymer | POLYQUATERNIUM-37 | 1 | 1 | 0.9 | 0.9 | 0.8 | 0.7 | 0.7 | 0.7 |
| (d) | Film former | VP/ DIMETHYLAMINOETHYLMETHACRYLATE COPOLYMER[1] | 0.6 | 0.6 | 0.6 | 0.6 | 0.6 | 0.6 | 0.6 | 0.6 |
| (e) | Silicone Polymer | ACRYLATES/ POLYTRIMETHYLSILOXYMETHACRYLATE COPOLYMER[2] | 0.1 | 0.1 | 0.1 | 0.1 | 0.1 | 0.05-0.1 | 0.1 | 0.1 |
| (f) | Oil | ISODODECANE and *RICINUS COMMUNIS* (CASTOR) SEED OIL | 8.2 | 8.2 | 8.2 | 8.2 | 5.2 | 1.6 | 1.7 | 1.7 |
| (h) | Fatty Alcohol | CETEARYL ALCOHOL | 1.5 | 1.5 | 1.5 | 1.5 | 1.5 | 1.5 | 1.5 | 1.5 |
| (i) | Thickening Agent | GELLAN GUM | | | | | | | | 0.1 |
| | Preservatives | PHENOXYETHANOL, and/or TOCOPHEROL, and/or ETHYLHEXYLGLYCERIN, and/or BENZOIC ACID | 0.9 | 0.9 | 0.9 | 0.9 | 0.9 | 0.9 | 0.8 | 1.1 |
| | Fragrance | FRAGRANCE | | | | | | | | 0.9 |
| (h) | Water | Water | QS to 100 | QS to 100 | QS to 100 | QS to 100 | QS to 100 | QS to 100 | QS to 100 | QS to 100 |

[1]commercially available under the tradename of COPOLYMER 845 from the company ISP.
[2]commercially available under the tradenames DOWSIL FA 4001 CM Silicone Acrylate or DOWSIL FA 4003 DM Silicone Acrylate or DOWSIL FA 4002 ID Silicone Acrylate or DOWSIL FA 4004 ID Silicone Acrylate from the Dow Chemical Company.

Example 2
(Comparative Compositions)

| | INCI US Name | Comp. 1 | Comp. 2 | Comp. 3 |
|---|---|---|---|---|
| Polyol | Glycerin | 2.5 | 2.5 | 45 |
| | PROPYLENE GLYCOL | | | 0.1 |
| Nonionic Surfactants | TRIDECETH-6 and PEG-180 | | | 2 |
| Cationic Surfactant | CETRIMONIUM CHLORIDE and/or BEHENTRIMONIUM CHLORIDE | 2.5 | 2.5 | 2.5 |
| Thickening Agent | HYDROXYPROPYL STARCH PHOSPHATE | | | 0.6 |
| Fatty Alcohol | CETEARYL ALCOHOL | 5.5 | 5.5 | 5 |
| Silicones | AMODIMETHICONE and DIMETHICONE | 3.5 | 3.5 | 6 |
| Plant based Extracts, Oils, Butters and/or Aromatic compounds | One or more of *MENTHA PIPERITA* (PEPPERMINT) OIL, *HELIANTHUS ANNUUS* (SUNFLOWER) SEED OIL, *PERSEA GRATISSIMA* (AVOCADO) OIL, *ROSMARINUS OFFICINALIS* (ROSEMARY) LEAF EXTRACT, *NIGELLA SATIVA* SEED OIL, *ZINGIBER OFFICINALE* (GINGER) ROOT EXTRACT, *CORIANDRUM SATIVUM* (CORIANDER) SEED OIL, *LINUM USITATISSIMUM* (LINSEED) SEED OIL, *ALOE BARBADENSIS* LEAF JUICE, and/or *RICINUS COMMUNIS* (CASTOR) SEED OIL | 0.4 | 0.1 | 0.1 |
| Miscellaneous (eg., fragrance preservatives, pH adjusters, solvents, emulsifiers and/or the like) | One or more of LACTIC ACID, SALICYLIC ACID, CITRIC ACID, PHENOXYETHANOL, SODIUM BENZOATE, POTASSIUM SORBATE, CHLORHEXIDINE DIHYDROCHLORIDE, TOCOPHEROL, FRAGRANCE, | 2.1 | 1.3 | 1.7 |

-continued

| Example 2 (Comparative Compositions) | | | | | |
|---|---|---|---|---|---|
| Water | ISOPROPYL ALCOHOL, and/or SORBITOL WATER | | QS to 100 | QS to 100 | QS to 100 |
| | INCI US Name | Comp. 4 | Comp. 5 | Comp. 6 | Comp. 7 |
| Polyols | GLYCERIN | | 0.1 | | <0.1 |
| | CAPRYLYL GLYCOL and/or PROPYLENE GLYCOL | | 0.7 | 0.3 | |
| Nonionic Surfactant | One or more of POLYSORBATE 60, TRIDECETH-12, C11-15 PARETH-7, TRIDECETH-6, LAURETH-9, UNDECETH-5, and/or UNDECETH-11 | 0.1 | 0.7 | 0.2 | |
| Amphoteric surfactants | STEARAMINE OXIDE | | 0.8 | | |
| Fatty Esters | CETYL ESTERS | 1 | 0.8 | | |
| Cationic Surfactants | BEHENTRIMONIUM CHLORIDE, and/or CETRIMONIUM CHLORIDE and/or QUATERNIUM-95, and/or QUATERNIUM-80 | 0.8 | 2 | 3 | 0.8 |
| Thickening Agents | HYDROXYETHYLCELLULOSE and GUAR HYDROXYPROPYLTRIMONIUM CHLORIDE | | 0.7 | | |
| Oils | ISODODECANE, and/or MINERAL OIL, and/or *GLYCINE SOJA* (SOYBEAN) OIL | 10 | 1.5 | | 1.5 |
| Fatty Alcohols | CETEARYL ALCOHOL and/or CETYL ALCOHOL and/or BENZYL ALCOHOL, and/or STEARYL ALCOHOL | 5 | 5.6 | 4.2 | 6 |
| Silicones | DIMETHICONE, and/or AMODIMETHICONE, and/or POLYSILICONE-15, and/or SILICONE QUATERNIUM-16, and/or CYCLOPENTASILOXANE, and/or DIMETHICONE PEG-8 MEADOWFOAMATE | 0.9 | 2.7 | 1.6 | 0.18 |
| Plant based Extracts, Oils, Butters and/or Aromatic compounds | One or more of *JOJOBA ESTERS*, *SIMMONDSIA CHINENSIS* (JOJOBA) SEED OIL, *ORYZA SATIVA* (RICE) EXTRACT, *ORYZA SATIVA* (RICE) SEED PROTEIN, *ALOE BARBADENSIS* LEAF JUICE, GALACTOARABINAN HYDROXYPROPYLTRIMONIUM CHLORIDE, HYDROGENATED OLIVE OIL UNSAPONIFIABLES, HYDROGENATED ETHYLHEXYL OLIVATE, PROPANEDIOL, PANTHENOL, *PRUNUS AMYGDALUS DULCIS* (SWEET ALMOND) OIL, KERATIN, HYDROLYZED KERATIN, *CYNARA SCOLYMUS* (ARTICHOKE) LEAF EXTRACT, *VANILLA PLANIFOLIA* FRUIT EXTRACT, *AGAVE TEQUILANA* LEAF EXTRACT, *MANGIFERA INDICA* (MANGO) SEED BUTTER, *CAMELLIA OLEIFERA* SEED OIL, *COCOS NUCIFERA* (COCONUT) OIL, *PYRUS MALUS* (APPLE) FRUIT EXTRACT, *MACADAMIA TERNIFOLIA* SEED OIL, HYDROXYPROPYLTRIMONIUM LEMON PROTEIN, *SACCHARUM OFFICINARUM* (SUGARCANE) EXTRACT, *CITRUS LIMON* (LEMON) FRUIT EXTRACT, *PYRUS MALUS* (APPLE) FRUIT EXTRACT, and/or *CAMELLIA SINENSIS* LEAF EXTRACT | 0.1 | 2 | 0.5 | 0.3 |
| Miscellaneous (e.g., fragrance | One or more of NIACINAMIDE, CYSTINE BIS-PG-PROPYL SILANETRIOL, BUTYLOCTANOL, | 1.5 | 2.7 | 2.5 | 0.4 |

-continued

| Example 2 (Comparative Compositions) | | | | | |
|---|---|---|---|---|---|
| preservatives, pH adjusters, solvents, emulsifiers, chelating agents, colors and/or the like) | HYDROLYZED VEGETABLE PROTEIN PG-PROPYL SILANETRIOL, ETHYLHEXYL METHOXYCINNAMATE, PHENOXYETHANOL, BHT, TOCOPHEROL, ISOPROPYL ALCOHOL, ISOBUTYLPARABEN, METHYLPARABEN, PROPYLPARABEN, BUTYLPARABEN, DISODIUM EDTA, SODIUM BENZOATE, CHLORHEXIDINE DIHYDROCHLORIDE, PYRIDOXINE HCl, ETHYLHEXYLGLYCERIN, IODOPROPYNYL BUTYLCARBAMATE, METHYLISOTHIAZOLINONE, CALCIUM GLUCONATE, GLUCONOLACTONE, CHLORPHENESIN, YELLOW 5, YELLOW 6, ACETIC ACID, CITRIC ACID, PHYTIC ACID, LACTIC ACID, BENZOIC ACID, SORBIC ACID, POTASSIUM SORBATE, PENTAERYTHRITYL TETRA-DI-T-BUTYL HYDROXYHYDROCINNAMATE, SODIUM CHLORIDE and/or FRAGRANCE | | | | |
| Water | WATER | QS to 100 | QS to 100 | QS to 100 | QS to 100 |

Example 3

(Assessment of Ex. R and Comp. 6)

Example Composition R (Ex. R) was evaluated in comparison to Comparative Composition 6 (Comp. 6). Specifically, about 8 gram samples for each of Example Composition R and Comparative Composition 6 were applied to a manikin's hair of the very curly hair type. The manikin's hair was washed before application of the samples. More specifically, the sample of Example Composition R was uniformly applied to a first half of the manikin's hair and the sample of Comparative Composition 6 was uniformly applied to the other half of the manikin's hair.

The application of compositions onto the hair of the manikin was evaluated to assess differences between Example Composition R and Comparative Composition 6. Example Composition R exhibited better slip and was easier to distribute on the hair than Comparative composition 6. Additionally, Example Composition R had a more substantive feel on the hand than Comparative Composition 6. Example composition R melted onto the hair during application. Comparative Composition 6 beaded up on the hair and required additional effort for detangling the hair after application of Comparative Composition 6. Comparative Composition 6 exhibited a white residue produced from the breaking of the film formed by Comparative Composition 6.

The manikin's hair was allowed to dry and was then evaluated again. The section of hair that received Example Composition R had closed ends and felt lightweight and conditioned, while still feeling that the hair was replenished with oil. Oil could be felt on the hair that received Example Composition R. The section of hair that received Comparative Composition 6 had open ends and appeared dry.

Example 4

(Assessment of Ex. C and Comp. 8)

Example Composition C (Ex. C) was evaluated in comparison to Comparative Composition 8 (Comp. 8), which is a commercially available product. The list of ingredients for Comp. 8 is provided below.

Water (Aqua), Polysorbate 20, Glycerin, Aloe Barbadensis Leaf Juice, Butylene Glycol, Calendula Officinalis Flower Extract, Citric Acid, Hydrolyzed Wheat Protein, Hydrolyzed Wheat Starch, Hydrolyzed Corn Starch Lavandula Angustifolia (Lavender) Flower/Leaf Stem Extract, Panthenol, Salvia Officinalis (Sage) Leaf Extract, Sodium PCA, Sodium Hyaluronate, Lonicera Caprifolium (Honeysuckle) Flower Extract, Lonicera Japonica (Honeysuckle) Flower Extract, Potassium Sorbate, Fragrance (Parfum), Caramel 1109B1420421.

About 8 gram samples for each of Example Composition C and Comparative Composition 8 were applied to a manikin's hair. The manikin's hair was washed before application of the samples. More specifically, the sample of Example Composition C was uniformly applied to a first half of the manikin's hair and the sample of Comparative Composition 8 was uniformly applied to the second half of the manikin's hair.

The application of compositions onto the hair of the manikin was evaluated to assess differences between Example Composition C and Comparative Composition 8. Example Composition C exhibited better slip and enabled easier detangling of the hair than Comparative Composition 8. Additionally, Example Composition C melted and then absorbed into the hair during application. The section of hair receiving Comparative Composition 8 had a shiny and wet appearance during application.

The manikin's hair was allowed to dry and was then evaluated again. The section of hair that received Example Composition R had good slip, felt conditioned, exhibited better frizz control, and better curl pick-up. The section of hair that received Comparative Composition 8 exhibited more individualized curls, more frizz, and left the hair feeling drier.

Example 5

(Assessment of Ex. C and Comp. 4)

Example Composition C (Ex. C) was evaluated in comparison to Comparative Composition 4 (Comp. 4). About 8 gram samples for each of Example Composition C and Comparative Composition 4 were applied to a manikin's hair. The manikin's hair was washed before application of the samples. More specifically, the sample of Example Composition C was uniformly applied to a first half of the manikin's hair and the sample of Comparative Composition 4 was uniformly applied to the other half of the manikin's hair.

The application of compositions onto the hair of the manikin was evaluated to assess differences between Example Composition C and Comparative Composition 4. Example Composition exhibited better slip and enabled easier detangling of the hair than Comparative Composition 4. Additionally, Example Composition C melted and then absorbed into the hair during application. The hair was harder to detangle and appeared very wet during the application of Comparative Composition 4. Comparative Composition 4 seemed to lay on top of the wet hair and readily transferred to the hands of the evaluator. In particular, Comparative Composition 4 took longer to absorb into the hair than Example Composition C.

The manikin's hair was allowed to dry and was then evaluated again. The section of hair that received Example Composition C had good slip, the curls were more elongated, and the hair had a higher hold. Example Composition C provides better frizz control and sealed ends as compared to Comparative Composition 4. The section of hair that received Comparative Composition 4 had soft curls, more frizz, and open ends. Additionally, the curls of the section of hair that received Comparative Composition 4 broke easily.

Example 6

(Assessment of Ex. T and Comp. 1)

Example Composition T (Ex. T) was evaluated in comparison to a Comparative Composition 1 (Comp. 1). About 8 gram samples for each of Example Composition T and Comparative Composition 1 were applied to a manikin's hair. The manikin's hair was washed before application of the samples. More specifically, the sample of Example Composition T was uniformly applied to a first half of the manikin's hair and the sample of Comparative Composition 1 was uniformly applied to the second half of the manikin's hair.

The application of compositions onto the hair of the manikin was evaluated to assess differences between Example Composition T and Comparative Composition 1. The section of hair that received Example Composition T had a lighter, more oil replenished feel than the hair that received Comparative Composition 1. Additionally, Example Composition T readily absorbed into the hair. Comparative Composition 1 felt heavier on the hair and provided a more topical feel. Comparative Composition 1 did not absorb into the hair easily, it lays on top of the hair instead of penetrating into the hair fibers.

The manikin's hair was allowed to dry and was then evaluated again. The section of hair that received Example Composition T had a more natural, softer feel. Example Composition T provided better slip to the hair, but was slightly more frizzy than the section of hair that received Comparative Composition 1. The section of hair that received Comparative Composition 1 had better curl pick-up, slightly crunchier curls, and a powdery feel. Comparative Composition 1 provided more control to the hair than Example Composition T.

Example 7

(Assessment of Ex. T and Comp. 3)

Example Composition T (Ex. T) was evaluated in comparison to a Comparative Composition 3 (Comp. 1). About 15 gram samples for each of Example Composition T and Comparative Composition 3 were applied to a manikin's hair. The manikin's hair was washed before application of the samples. More specifically, the sample of Example Composition T was uniformly applied to a first half of the manikin's hair and the sample of Comparative Composition 3 was uniformly applied to the second half of the manikin's hair.

The application of compositions onto the hair of the manikin was evaluated to assess differences between Example Composition T and Comparative Composition 3. Example Composition T was easier to distribute onto the hair than Comparative Composition 3. Both Example Composition T and Comparative Composition 3 enabled easy detangling of hair during application. Comparative Composition 3 absorbed easily into the hair, but had a very thick, petrolatum feel.

The manikin's hair was allowed to dry and was then evaluated again. The section of hair that received Example Composition T had a smooth and dry feeling. Example Composition T provided light weight control and enabled fingers to glide easy through the hair. The section of hair that received Comparative Composition 1 had a heavier coating that was sticky/tacky and readily transferred to the hands of the evaluator. Additionally, Comparative Composition 3 left the hair feeling heavier.

Example 8

(Assessment of Ex. T and Comp. 2)

Example Composition T (Ex. T) was evaluated in comparison to a Comparative Composition 2 (Comp. 2). About 8 gram samples for each of samples of Example Composition T and Comparative Composition 2 were applied to a manikin's hair. The manikin's hair was washed before application of the samples. Specifically, the sample of Example Composition T was uniformly applied to a first half of the manikin's hair and the sample of Comparative Composition 2 was uniformly applied to the other half of the manikin's hair.

The application of compositions onto the hair of the manikin was evaluated to assess differences between Example Composition T and Comparative Composition 2. Both Example Composition T and Comparative Composition 2 were easy to distribute and enabled easy detangling of the hair during application. Example Composition T absorbed into the hair easily, without leaving a residue. Comparative Composition 2 beaded on the hair and did not absorb into the hair.

The manikin's hair was allowed to dry and was then evaluated again. The section of hair that received Example Composition T had no residue on the hair and exhibited good slip. Example Composition T provided a flexible hold, but allowed for slightly more frizz than Comparative Composition 2. The section of hair that received Comparative Composition 2 felt dry. Comparative Composition 2 produced a hard film that exhibited hair control, but resulted in a white residue on the hair.

Example 9

(Evaluation of Rheological Properties of Ex. U)

The unique rheological characteristics of Exemplary Composition U was assessed by evaluating the viscosity of such hair cosmetic composition. Specifically, the viscosities of the sample of Example Composition U and the diluted sample of Example Composition U were measured using a rheometer (DHR-2, TA instruments, New Castle, DE, USA) and 40 mm parallel plate geometry. A 1 mm gap between the parallel plates was chosen. All tests were conducted at a temperature of 25° C. and atmospheric pressure. The sample was subjected to shear ramp starting from 0.1 1/s to 1000 1/s within a 300 second period. The time interval between data points was 1 s. The shear stress response was recorded for every data point.

Figure 2:
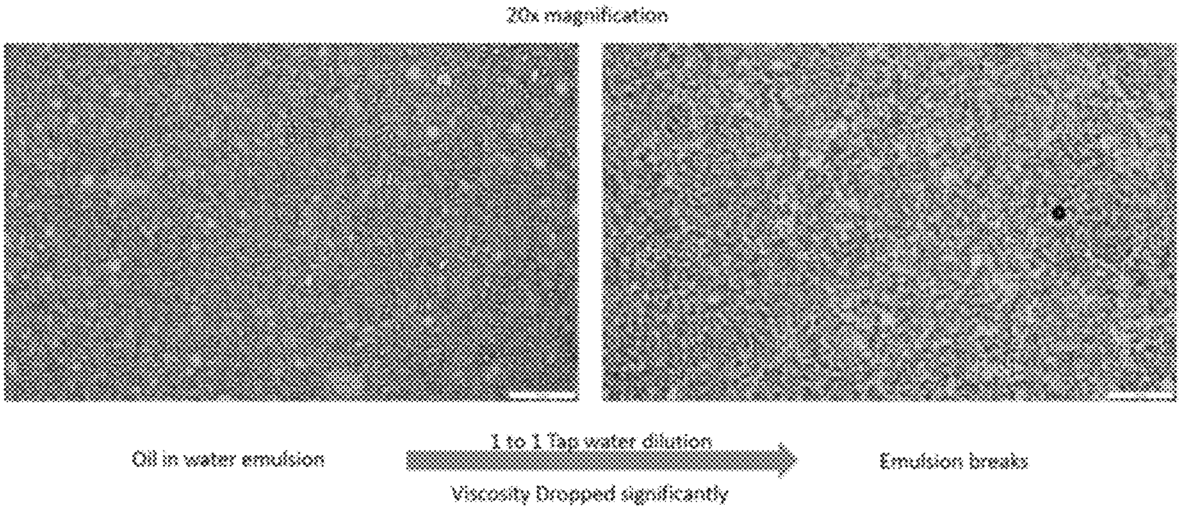
FIG. 2 is images of the emulsion of a non-limiting exemplary composition before and after dilution.

The viscosity of the sample of Example Composition U was greater than the viscosity of the diluted sample of Example Composition U. A graph illustrating the viscosities of the sample of Example Composition U and the diluted sample of Example Composition U as the shear rate was increased is shown in FIG. 1. As seen in FIG. 2, the emulsion of the diluted sample of Example Composition U (1:1 dilution of Example Composition U to water) was broken. While it presently believed that some embodiments of the hair cosmetic compositions do not require dilution to transform from a cream to an oil, FIGS. 1 and 2 are useful for illustrating the uniqueness of the rheological characteristics of the hair cosmetic compositions and how the cream transforms to an oil when applied onto wet hair. Additionally, as seen in FIGS. 1 and 2, the rheological characteristics of Exemplary Composition U was different from traditional compositions having an emulsion.

Figure 3:
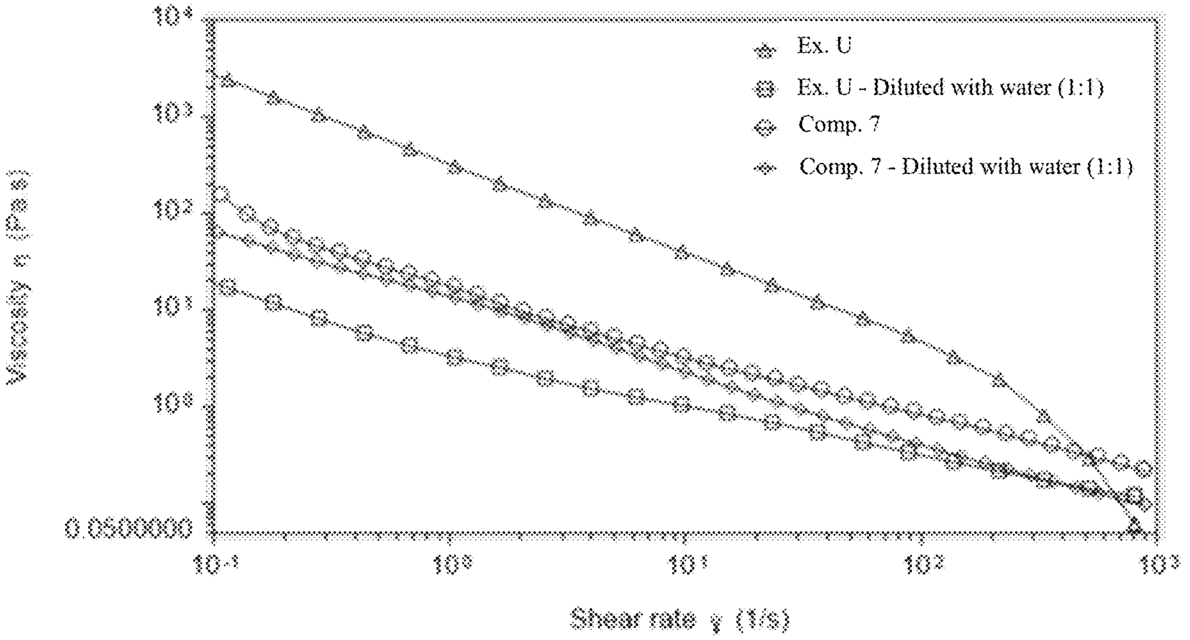
FIG. 3 is a graph of the viscosity over a range of shear stress rates for a non-limiting exemplary composition, a comparative composition, and diluted samples thereof in accordance with aspects of the disclosure.

Comparative Composition 7 was evaluated under the same conditions as Example Composition U to provide a comparison of the rheological properties of Example Composition U with Comparative Composition 7. FIG. 3 is a graph illustrating the viscosities of the sample of Example Composition U, the diluted sample of Example Composition U, a sample of Comparative Composition 7, and a diluted sample of Comparative Composition 7 as the shear rate was increased.

Example 10

(Emulsion of Exemplary Composition)

It is believed that certain exemplary compositions presented in Example 1 produce emulsions with an aqueous phase and an oil phase having the following ingredients as specified in the following table.

| Phase: A = water, B = oil | US INCI compound name |
|---|---|
| B | *RICINUS COMMUNIS* (CASTOR) SEED OIL |
| B | CETEARYL ALCOHOL |
| B | CETYL ESTERS (and) CETYL ESTERS |
| B | ISOPROPYL MYRISTATE |
| A | FRAGRANCE |
| A | VP/DIMETHYLAMINOETHYLMETHACRYLATE COPOLYMER |
| B | POLYQUATERNIUM-37 |
| A | GELLAN GUM |
| A | PHENOXYETHANOL |
| B | BENZOIC ACID |
| B | ACRYLATES/POLYTRIMETHYLSILOXY-METHACRYLATE COPOLYMER |
| A | WATER |
| A | BUTYLENE GLYCOL |
| A | GLYCERIN |
| A | ETHYLHEXYLGLYCERIN |
| A | CAPRYLYL GLYCOL |
| A | GLYCERYL STEARATE (and) PEG-100 STEARATE |

The invention claimed is:

1. A leave-in hair conditioning and styling composition comprising:
- (a) two or more polyols comprising:
  - (i) about 1 to about 8 wt. % of a glycol, and
  - (ii) about 2 to about 10 wt. % of glycerin;
- (b) about 0.5 to about 5 wt. % of a nonionic surfactant;
- (c) about 10 to about 28 wt. % of a fatty ester;
- (d) about 0.1 to about 3 wt. % of VP/dimethylaminoethylmethacrylate copolymer;
- (e) about 0.05 to about 2 wt. % of acrylates/polytrimethylsiloxymethacrylate copolymer;
- (f) about 0.5 to about 12 wt. % of an oil; and
- (g) water,
  - wherein all weight percentages are based on the total weight of the composition; and
    - wherein the composition has a pH of about 3.5 to about 6,
    - the composition is formulated as a leave-in hair conditioning and styling composition, and
    - the composition is a cream at rest having a viscosity of about 20 to about 500 Pa·s at 25° C., and upon application of shear within a rate range of about 1 to about 10 $s^{-1}$ transforms into an oil having a viscosity of about 0.01 to about 10 Pa·s at 25° C.

2. A leave-in hair conditioning and styling composition comprising:
- (a) about 4 to about 32 wt. % of two or more polyols comprising:
  - (i) about 1 to about 8 wt. % of a glycol selected from ethylene glycol, propylene glycol, butylene glycol, hexylene glycol, pentylene glycol, diethylene glycol, dipropylene glycol, 1,3 propanediol, ethylhexylglycerin, or mixtures thereof, and
  - (ii) about 2 to about 8 wt. % of glycerin;
- (b) about 0.5 to about 5 wt. % of a nonionic surfactant;
- (c) about 10 to about 30 wt. % of a fatty ester;
- (d) about 0.1 to about 5 wt. % of a film VP/dimethylaminoethylmethacrylate copolymer;
- (e) about 0.05 to about 4 wt. % of acrylates/polytrimethylsiloxymethacrylate copolymer;
- (f) about 0.5 to about 5 wt. % of plant oil;
- (g) water;
- (h) about 0.5 to about 5 wt. % of a fatty alcohol; and
- (i) about 0.1 to about 3 wt. % of polyquaternium-37, wherein all weight percentages are based on a total weight of the composition; and wherein the composition is an oil-in-water emulsion, the composition has a pH of about 3.5 to about 6, the composition is formulated as a leave-in hair conditioning and styling composition, and the composition is a cream at rest having a viscosity of about 20 to about 500 Pa·s at 25° C., and upon application of shear within a rate range of about 1 to about 10 $s^{-1}$ transforms into an oil having a viscosity of about 0.01 to about 10 Pa·s at 25° C.

3. A method of styling hair comprising:

(I) applying the composition of claim 1 to hair; and (II) styling the hair.

4. A leave-in hair conditioning and styling composition comprising:

(a) about 4 to about 20 wt. % of two or more polyols comprising:

(i) about 1 wt. % or more of a glycol, and (ii) about 2 wt. % or more of glycerin;

(b) about 0.5 to about 10 wt. % of a nonionic surfactant;

(c) about 2 to about 35 wt. % of a fatty ester;

(d) about 0.1 to about 7 wt. % of VP/dimethylaminoethylmethacrylate copolymer;

(e) about 0.05 to about 10 wt. % of a silicone acrylate polymer selected from acrylates/dimethicone copolymer, acrylates/stearyl acrylate/dimethicone acrylates copolymer, acrylates/behenyl acrylate/dimethicone acrylates copolymer, acrylates/polytrimethylsiloxymethacrylate copolymer, poly (dimethylsiloxane)-g-poly(isobutyl methacrylate), or mixtures thereof;

(f) about 0.5 to about 12 wt. % of an oil;

(g) water; and (h) about 0.5 to about 5 wt. % of a fatty alcohol, wherein all weight percentages are based on a total weight of the composition; and wherein the composition has a pH of about 3.5 to about 6, the composition is formulated as a leave-in conditioning and styling composition, the composition is an oil-in-water emulsion, and the composition is a cream at rest having a viscosity of about 20 to about 500 Pa·s at 25° C., and upon application of shear within a rate range of about 1 to about 10 $s^{-1}$ transforms into an oil having a viscosity of about 0.01 to about 10 Pa·s at 25° C.

5. The composition of claim 4 further comprising polyquaternium-37.

6. The composition of claim 2, wherein the fatty esters are selected from cetyl palmitate, cetyl stearate, cetyl esters, myristyl myristate, myristyl stearate, cetyl myristate, stearyl stearate, glyceryl stearate, propylene glycol dicaprylate/dicaprate, cetearyl ethylhexanoate, isopropyl isostearate, n-propyl myristate, isopropyl myristate, hexyl laurate, hexadecyl isostearate, hexydecyl laurate, hexyldecyl octanoate, n-propyl palmitate, isopropyl palmitate, or mixtures thereof.

7. The composition of claim 2, wherein the oil is a plant oil selected from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, ricinus communis seed oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, or mixtures thereof.

8. The composition of claim 2, wherein the fatty alcohol has from 12 to 22 carbon atoms.

9. The composition of claim 8, wherein the fatty alcohol is cetearyl alcohol.

10. A method of styling hair comprising:

(I) applying the composition of claim 2 to hair; and (II) styling the hair.

11. The composition of claim 1, further comprising:

(h) about 0.5 wt. % to about 8 wt. % of a fatty alcohol.

12. The composition of claim 11, wherein the fatty alcohol is cetearyl alcohol.

13. The composition of claim 1, further comprising:

(i) a quaternary ammonium polymer.

14. The composition of claim 13, wherein the quaternary ammonium polymer is polyquaternium-37.

15. The composition of claim 1, wherein the composition is an oil-in-water emulsion.

16. The composition of claim 4, wherein the glycol is butylene glycol.

17. A method of styling hair comprising:

(I) applying the hair composition of claim 2 to hair; and (II) styling the hair.

* * * * *